(12) United States Patent
Nordmeyer et al.

(10) Patent No.: US 11,272,916 B2
(45) Date of Patent: *Mar. 15, 2022

(54) SYSTEMS, DEVICES AND METHODS FOR AFFIXING SOFT TISSUE TO BONE

(71) Applicants: Michael William Nordmeyer, Pittstown, NJ (US); Daniel J. Smith, Little Egg Harbor, NJ (US)

(72) Inventors: Michael William Nordmeyer, Pittstown, NJ (US); Daniel J. Smith, Little Egg Harbor, NJ (US)

( * ) Notice: Subject to any disclaimer, the term of this patent is extended or adjusted under 35 U.S.C. 154(b) by 228 days.

This patent is subject to a terminal disclaimer.

(21) Appl. No.: 16/413,161

(22) Filed: May 15, 2019

(65) Prior Publication Data
US 2019/0261976 A1    Aug. 29, 2019

Related U.S. Application Data

(63) Continuation of application No. 15/439,272, filed on Feb. 22, 2017, now Pat. No. 10,307,153.
(Continued)

(51) Int. Cl.
*A61B 17/04* (2006.01)
*A61B 17/88* (2006.01)
(Continued)

(52) U.S. Cl.
CPC ........ *A61B 17/0401* (2013.01); *A61B 17/862* (2013.01); *A61B 17/8605* (2013.01);
(Continued)

(58) Field of Classification Search
CPC ............ A61B 17/0401; A61B 17/8605; A61B 17/862; A61B 17/863; A61B 17/8635;
(Continued)

(56) References Cited

U.S. PATENT DOCUMENTS

| 2,092,682 | A | 9/1937 | Roske |
| 4,793,335 | A | 12/1988 | Frey et al. |

(Continued)

*Primary Examiner* — Mohamed G Gabr
(74) *Attorney, Agent, or Firm* — Doherty IP Law Group LLC

(57) ABSTRACT

A system for fastening soft tissue to bone includes a bone screw having a threaded shaft and a screw head having an underside with malleable protuberances that project toward a distal end of the threaded shaft. A fixation plate is coupled with the threaded shaft. The fixation plate has a proximal face that opposes the underside of the screw head, a distal face that faces away from the underside of the screw head, an outer peripheral edge that extends between the proximal and distal faces, a central opening for receiving the threaded shaft, and protrusions spaced from one another around the outer peripheral edge that extend distally beyond the distal face of the fixation plate. The system includes an insertion tool having a handle and a tubular shaft extending distally from the handle. The tubular shaft has a proximal shaft section having an inner diameter that closely matches an outer diameter of the screw head, and a distal shaft section having an inner surface with a groove that seats the outer peripheral edge of the fixation plate for releasable retaining the fixation plate within the distal shaft section. A cartridge contains the bone screw and the fixation plate coupled with the bone screw. The cartridge includes a proximal end that seats the screw head and a distal end that seats the fixation plate of the bone screw.

22 Claims, 17 Drawing Sheets

Related U.S. Application Data

(60) Provisional application No. 62/298,324, filed on Feb. 22, 2016.

(51) Int. Cl.
  *A61B 17/86* (2006.01)
  *A61B 90/00* (2016.01)

(52) U.S. Cl.
  CPC ........ *A61B 17/865* (2013.01); *A61B 17/8695* (2013.01); *A61B 17/8891* (2013.01); *A61B 17/8894* (2013.01); *A61B 17/863* (2013.01); *A61B 17/8635* (2013.01); *A61B 2017/044* (2013.01); *A61B 2017/0409* (2013.01); *A61B 2017/0416* (2013.01); *A61B 2090/0807* (2016.02); *A61B 2090/0808* (2016.02)

(58) Field of Classification Search
  CPC .............. A61B 17/865; A61B 17/8695; A61B 17/8891; A61B 17/8894; A61B 2017/0409; A61B 2017/0416; A61B 2017/044; A61B 2090/0807; A61B 2090/0808
  See application file for complete search history.

(56) References Cited

U.S. PATENT DOCUMENTS

| | | |
|---|---|---|
| 4,872,451 A | 10/1989 | Moore et al. |
| 4,988,351 A | 1/1991 | Paulos et al. |
| 5,013,316 A | 5/1991 | Goble et al. |
| 5,314,427 A | 5/1994 | Goble et al. |
| D374,482 S | 10/1996 | Goble et al. |
| 5,840,078 A | 11/1998 | Yerys |
| 5,961,521 A | 10/1999 | Roger |
| 6,056,751 A | 5/2000 | Fenton, Jr. |
| 6,117,139 A | 9/2000 | Shino |
| 6,383,187 B2 | 5/2002 | Tormala |
| 6,464,706 B1 | 10/2002 | Winters |
| 6,632,245 B2 | 10/2003 | Kim |
| 6,746,191 B2 | 6/2004 | Edland |
| 7,604,659 B2 | 10/2009 | Lee |
| 8,894,685 B2 | 11/2014 | Mickiewicz et al. |
| 10,307,153 B2 | 6/2019 | Nordmeyer et al. |
| 2003/0105465 A1 | 6/2003 | Schmieding et al. |
| 2005/0228387 A1* | 10/2005 | Paul .................. A61B 17/86 606/246 |
| 2006/0149266 A1 | 7/2006 | Cordasco |
| 2008/0086131 A1 | 4/2008 | Daly et al. |
| 2008/0255622 A1 | 10/2008 | Mickiewicz et al. |
| 2010/0094356 A1* | 4/2010 | Varela ................. A61B 17/862 606/304 |
| 2011/0040339 A1 | 2/2011 | Solomon et al. |
| 2014/0257412 A1 | 9/2014 | Patty et al. |

\* cited by examiner

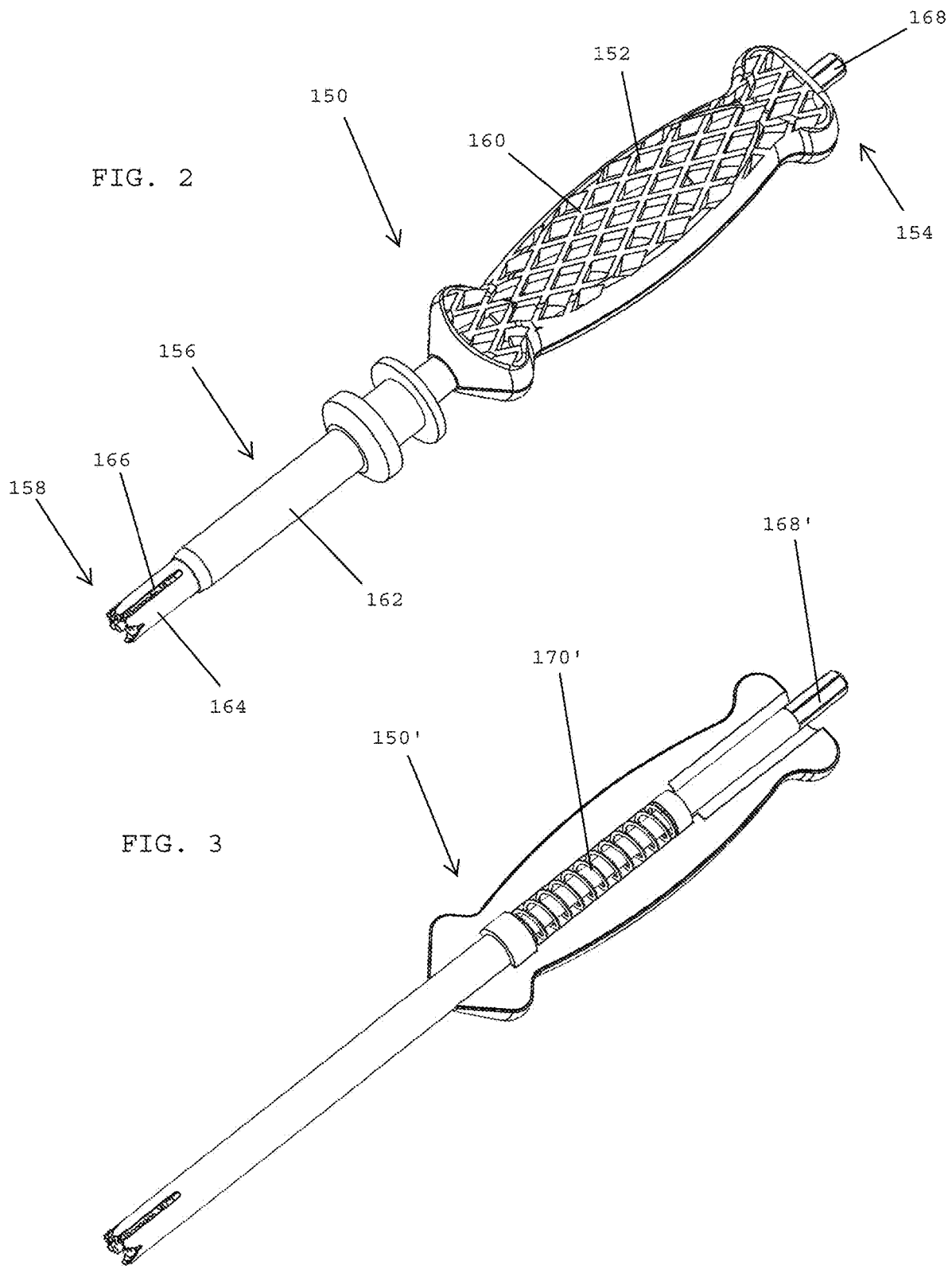

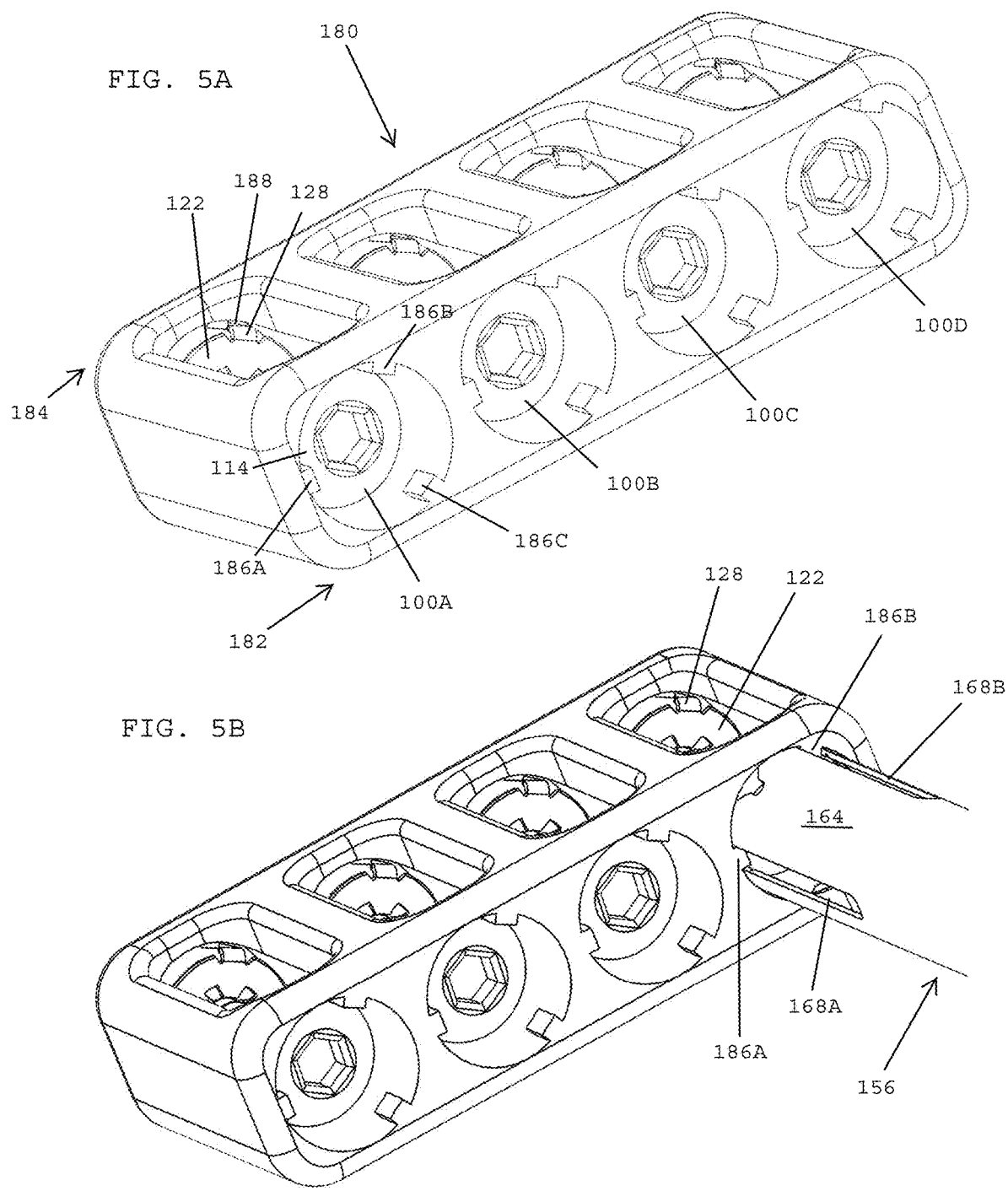

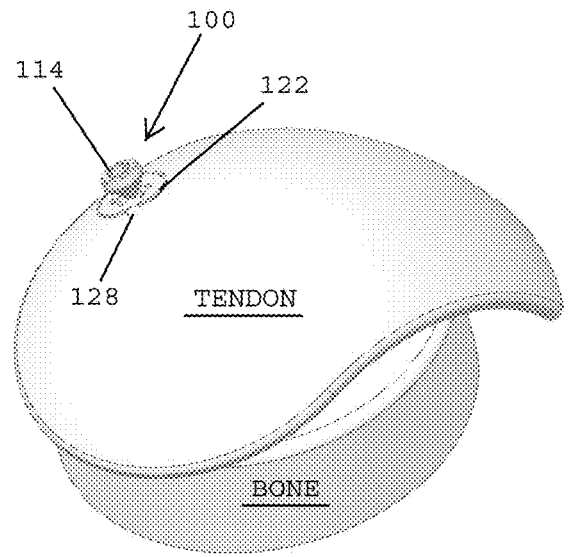
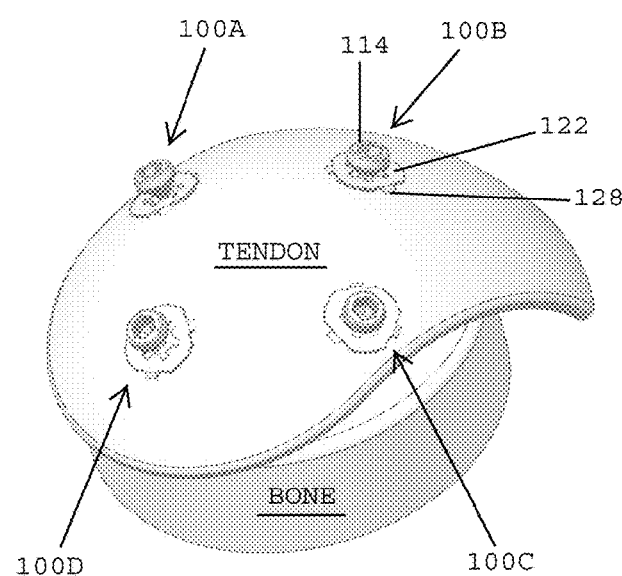
FIG. 8A
FIG. 8B
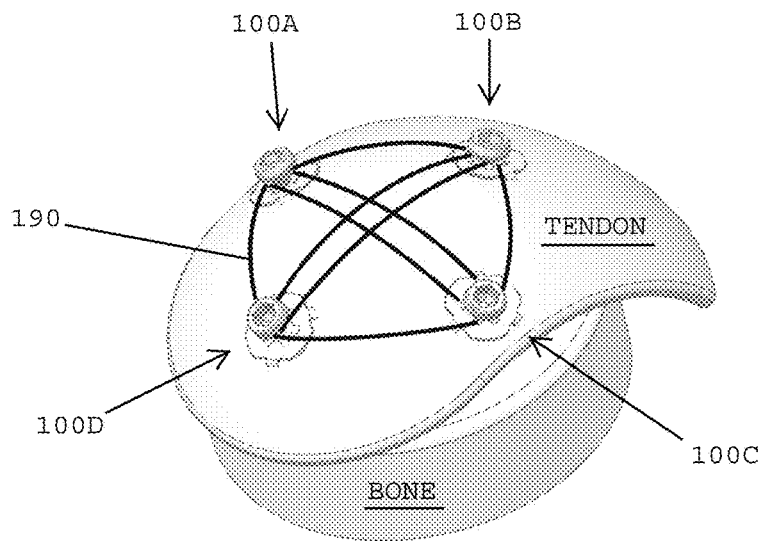
FIG. 8C

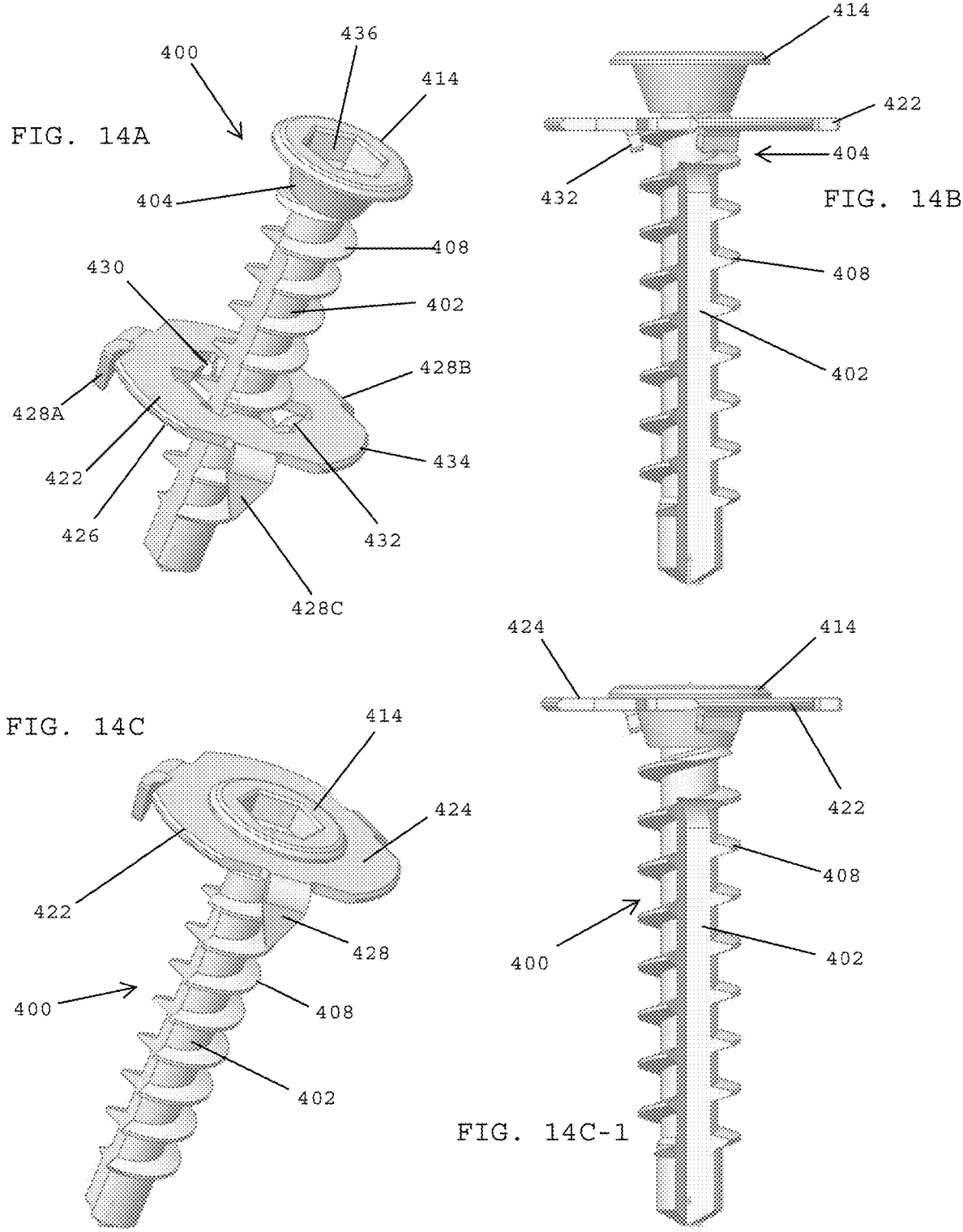

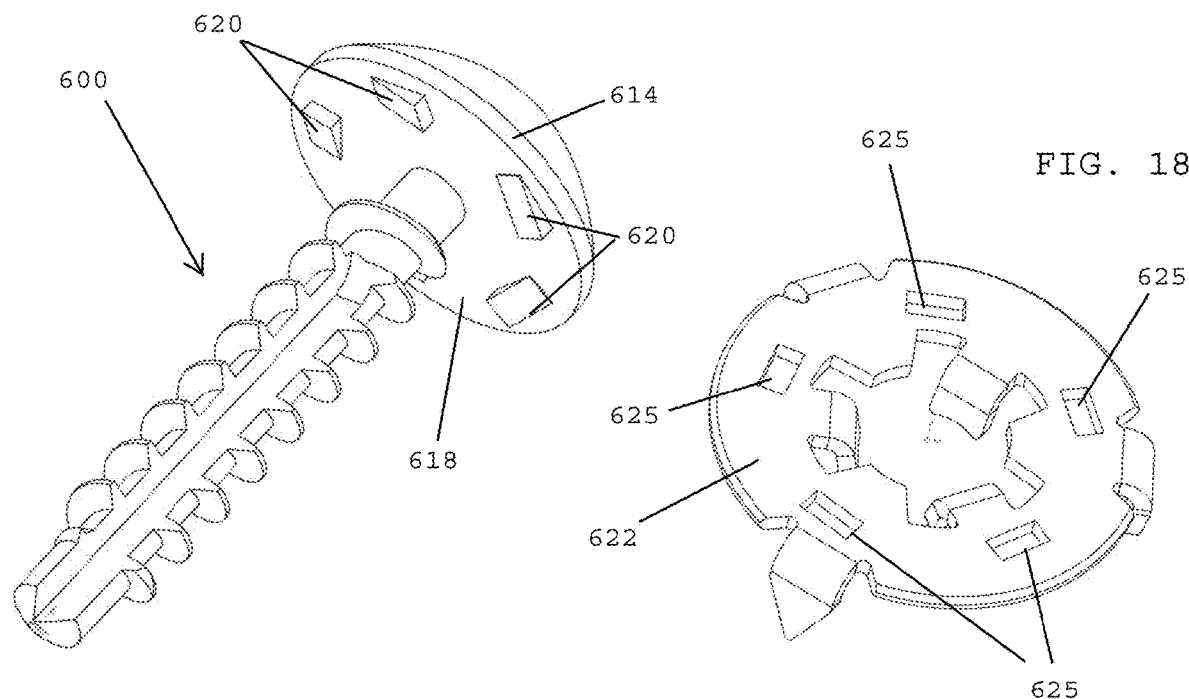
FIG. 18
FIG. 17
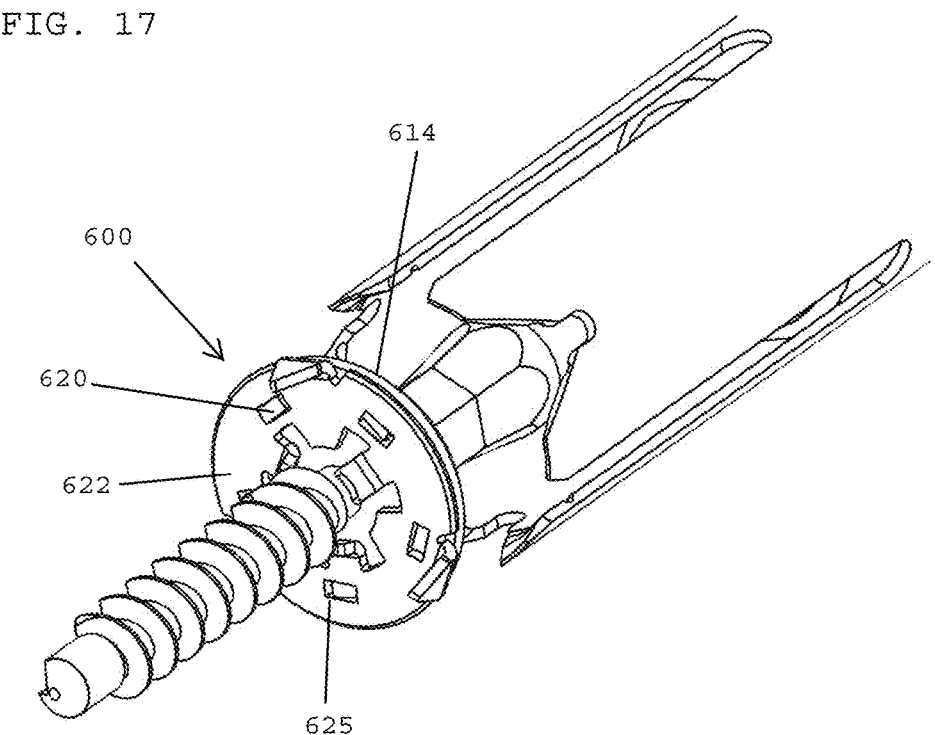
FIG. 19

SYSTEMS, DEVICES AND METHODS FOR AFFIXING SOFT TISSUE TO BONE

CROSS-REFERENCE TO RELATED PATENT APPLICATIONS

The present patent application is a continuation of U.S. patent application Ser. No. 15/439,272, filed Feb. 22, 2017, which claims benefit of U.S. Provisional Patent Application Ser. No. 62/298,324, filed Feb. 22, 2016, the disclosures of which are hereby incorporated by reference herein.

BACKGROUND OF THE INVENTION

Field of the Invention

The present patent application is generally related to medical devices and surgical procedures, and is more specifically related to non-invasive medical devices and surgical procedures use for affixing soft tissue, such as tendons, to bone.

Description of the Related Art

There are many different types of bone screws that require pre-drilling into bone before the bone screws are anchored in the bone. For example, general screws and general washers used for attaching soft tissue to bone, as well as metallic devices and plates to bone, all typically require pre-drilling specific sized holes into the hard cortical bone prior to insertion of a fastening screw type devices, or pre-drilling and wedging/pinching/sewing tissue into these holes to connect or attach tissue to bone during surgery.

There are also numerous systems through which tubes are pasted, drills are inserted and fastening devices are moved in and out these tubes to allow access and to maintain positional alignment.

Both of these examples of the current technologies require multiple steps to achieve fixation of tissue to hard cortical bone such as that found in the upper arms or legs which is not only hard but can fracture, split or crack if the proper ratio between the "pre-drill" drill bit step and when the screw or wedge type fastener is turned or hammered into the "pre-drilled" hole. They also utilize age old methods such as standard drill bits of various shapes and sizes and typical electric hand drills, pins, hammers and screw drivers to accomplish orthopedic surgeries.

"Pre-drilling" also creates unwanted bone chips which need to be controlled and removed from the surgical area to prevent sand like grit from possible entry into joints or between sliding surfaces causing irritation and post-operative pain.

The "pre-drilling" step and multiple in-and-out actions through tubes is also time consuming and may lead to movement or misplacement of intended holes. Other concerns include the rising costs of health care and surgical procedures as operating room costs continue to increase. Thus, simplifying surgical procedures to decrease the lengths of surgical procedures and/or decrease the rate of medical complications is extremely important.

In spite of the above advances, there remains a need for improved, non-invasive systems, devices and methods for affixing soft tissue to bone.

SUMMARY OF THE INVENTION

In one embodiment, a system for fastening soft tissue to bone desirably includes a bone screw having a threaded shaft with a proximal end and a distal end, a screw head secured to the proximal end of the threaded shaft, and a self-tapping tip located at the distal end of the threaded shaft. In one embodiment, the self-tapping tip located at the distal end of the threaded shaft desirably includes an angled or fluted tip having at least one sharpened edge.

In one embodiment, the threaded shaft of the bone screw preferably has an elongated groove devoid of threads that extends between the distal and proximal ends of the threaded shaft for collecting bone chips as the bone screw is rotated and/or advanced into bone and/or allowing the chips to be brought to the surface below the tissue being fastened as said bone screw is advanced into bone.

In one embodiment, the underside of the screw head preferably has one or more malleable protuberances that project toward the proximal face of the fixation plate.

In one embodiment, the system desirably includes a fixation plate coupled with the threaded shaft, the fixation plate having a central opening for receiving the threaded shaft of the bone screw and protrusions that extend distally from the fixation plate.

In one embodiment, the fixation plate has a proximal face that opposes an underside of the screw head, a distal face that faces away from the underside of the screw head, and an outer perimeter edge that extends between the proximal face and the distal face. In one embodiment, the protrusions are spaced from one another about the outer peripheral edge of the fixation plate and extend distally from the distal face of the fixation plate. In one embodiment, the spaced protrusions on the fixation plate preferably have sharpened lower ends for biting into soft tissue and/or bone.

In one embodiment, the central opening of the fixation plate has an outer perimeter, and the fixation plate may include guide flanges positioned around the outer perimeter of the central opening for engaging the threaded shaft of the bone screw. In one embodiment, the guide flanges extend distally from the distal face of the fixation plate. In one embodiment, the guide flanges project into the central opening of the fixation plate.

In one embodiment, the bone screw and the fixation plate may be made of biocompatible materials such as metal, stainless steel and titanium.

In one embodiment, the system desirably includes an insertion tool having a handle and a tubular shaft extending distally from the handle. In one embodiment, the tubular shaft preferably has a proximal shaft section having an inner diameter that closely matches an outer diameter of the screw head, and the tubular shaft has a distal shaft section having an inner surface with a groove that seats the outer peripheral edge of the fixation plate for retaining the fixation plate within the distal shaft section until the retaining plate is contacted by the underside of the screw head.

In one embodiment, the distal shaft section preferably includes a plurality of spaced, elongated slots that extend along the length of the tubular shaft. In one embodiment, the spaced, elongated slots are open at the distal-most end of the tubular shaft. In one embodiment, the spaced protrusions of the fixation plate are disposed within the spaced, elongated slots.

In one embodiment, the insertion tool preferably has castling or gripping teeth projecting from the distal-most end of the tubular shaft. The tubular shaft of the insertion tool may be may of biocompatible materials such as plastic, polymers, and metal such as stainless steel and titanium.

In one embodiment, a screw head of a bone screw has a top side with a tool opening. In one embodiment, the insertion tool has a rotatable tool bit having a proximal end projecting from a proximal end of the handle and a distal end disposed within the tool opening of the screw head. In one embodiment, the tool bit is configured to be rotated for rotating the screw head and the threaded shaft about a longitudinal axis of the threaded shaft. A power tool may be used for engaging the proximal end of the tool bit and rotating the tool bit.

In one embodiment, a system for fastening soft tissue to bone preferably includes a bone screw having a threaded shaft with a proximal end and a distal end, a screw head secured to the proximal end of the threaded shaft, the screw head having an underside with malleable protuberances that project toward the distal end of the elongated shaft, and a fixation plate coupled with the threaded shaft, the fixation plate including a proximal face that opposes the underside of the screw head, a distal face that faces away from the underside of the screw head, an outer peripheral edge that extends between the proximal and distal faces, a central opening for receiving the threaded shaft of the bone screw, and protrusions spaced from one another around the outer peripheral edge that extend distally beyond the distal face of the fixation plate. In one embodiment, the system includes an insertion tool having a handle and a tubular shaft extending distally from the handle, whereby the tubular shaft has a proximal shaft section having an inner diameter that closely matches an outer diameter of the screw head, and wherein the tubular shaft has a distal shaft section having an inner surface with a groove that seats the outer peripheral edge of the fixation plate for releasably retaining the fixation plate within the distal shaft section.

In one embodiment, a system for fastening soft tissue to bone preferably includes a bone screw having a threaded shaft with a proximal end, a distal end, a longitudinal axis extending between the proximal and distal ends of the threaded shaft, a screw head secured to the proximal end of the threaded shaft, the screw head having an underside with malleable protuberances that project toward the distal end of the elongated shaft, and a self-tapping tip located at the distal end of the threaded shaft.

In one embodiment, the system includes a fixation plate coupled with the threaded shaft, the fixation plate including a proximal face that opposes the underside of the screw head, a distal face that faces away from the underside of the screw head, an outer peripheral edge that extends between the proximal and distal faces, a central opening for receiving the threaded shaft of the bone screw, and protrusions spaced from one another around the outer peripheral edge of the fixation plate that extend distally beyond the distal face of the fixation plate.

In one embodiment, the system preferably includes an insertion tool having a handle and a tubular shaft extending distally from the handle, whereby the tubular shaft has a proximal shaft section having an inner diameter that closely matches an outer diameter of the screw head and a distal shaft section having an inner surface with a groove that seats the outer peripheral edge of the fixation plate for releasably retaining the fixation plate within the distal shaft section. The distal shaft section preferably has a plurality of spaced, elongated slots that extend along the length of the tubular shaft and that are open at a distal-most end of the tubular shaft, whereby the spaced protrusions of the fixation plate are disposed within the spaced, elongated slots of the distal shaft section.

One embodiment of the present application discloses a one step, one piece, self-tapping, self-centering, self-deploying, non-rotational, self-contained soft tissue to bone fastening system which does not require a "pre-drilled" hole step. In one embodiment, a system includes one or more pre-loaded or reloadable type tissue fastening devices which are retained and positional centered within the spring like distal tip of the system shaft while being slidably disconnected from the drive pin to prevent accidental head rotation or linear fastener movement prior to its intended insertion into tissue/bone.

In one embodiment, the self-tapping, self-deploying tissue fastener includes a proximal head and a distal tip, wherein proximal to the distal tip is located a fastener fixation ring that provides multiple functions. In one embodiment, the distal tip of the fastener has an angled or fluted tip of some length with at least one sharpened edge and the at least some or all of the linear fastener length between the distal tip and proximal head having at least one type of radial, helical or spiral features of various pitches which have a depth less than or greater than that of the pointed distal tip. In one embodiment, the linear length could be groove-less or could contain at least one groove or partial groove along the length. The linear length may also have at least one flat or multiple flats of various depths which desirably reduce the overall major thread diameter and create gaps linear or spiral voids to collect bone chips or reduce frictional interference between the fastener and the hard cortical bone. The angle of the drill tip may facilitate better initial starting in hard bone and minimize "walking" of the system from its intended location.

In one embodiment, the voids within the linear length need not be symmetrical or uniform. The voids may be angled along the length for the purpose of creating equivalent or changing ratios along the length between the furthest distal tip and the proximal fastener head.

In one embodiment, the major thread diameter is less than the drill tip diameter by about say 0.005 inches or less due to either linear voids or choice of diameters for a given procedure.

In one embodiment, the major thread diameter is less than the drill tip diameter by between about 0.005 and 0.05 inches due to either linear voids or choice of diameters for a given procedure.

In one embodiment, the major thread diameter is less than the drill tip diameter by between about 0.01 and 0.04 inches and more preferably about 0.02 and 0.03 inches due to either linear voids or choice of diameters for a given procedure.

In one embodiment, the major thread diameter is equal to the drill tip diameter, or about a 1-to1 ratio.

In one embodiment, the major thread diameter is effectively greater than the drill tip diameter by about 0.005 inches or less due to either linear voids or choice of diameters for a given procedure.

In one embodiment, the major thread diameter is effectively greater than the drill tip diameter by between about 0.005 and 0.05 inches due to either linear voids or choice of diameters for a given procedure.

In one embodiment, the major thread diameter is effectively greater than the drill tip diameter by between about 0.01 and 0.04 inches and more preferably between about 0.02 and 0.03 inches due to either linear voids or choice of diameters for a given procedure.

In one embodiment, the fixation ring located proximal to the distal tip of the fastener desirably has formed features centrally located to the fixation ring which are designed to guide and position the linear length of the fastener shaft as well as having one or more end features which are directionally substantially parallel to the center line of the linear length of the fastener shaft yet located near or equal to an inner diameter of the fixation ring. In one embodiment, the protruding end features on the fixation ring may be of a variety of designs or shapes such as rounded, pointed, oval, square, etc., and may have lengths at least the thickness of the fixation ring or be designed to mate with the threads or have features or designs so as to not engage with the linear shaft and the substantially parallel protrusions may be either straight or angled and may have features designed to direct their movement when placed under pressure by the fastener head.

In one embodiment, the surgical fasteners disclosed herein may be self deploying. This self-deployment feature is controlled by the spring like distal tip of the system shaft, which contains an internal feature that may be positioned or located elsewhere along the tubular shaft which is designed to be either mating, similar to or dissimilar to the external feature on the outer most perimeter edge or edges of the fixation ring. The security of the fixation ring is controlled by the tubular shaft material, the tubular shaft wall thickness, the length and width of the slots in the distal end of tubular shaft or the design of the above mentioned internal and external features of the tubular shaft or fixation ring respectively of any combination thereof. These internal and external features of the tubular shaft or fixation ring may be designed to facilitate or have control over the degree of force required either for loading or self deployment of the fastener. It is understood by those in the art that a tubular shaft does not need to be circular in cross sectional shape. It is also understood by those in the art that both the tubular shaft and fastener need not be made of metal such as Ti, Stainless steel and could be made from plastic such as PEEK and or Poly carbonite or reinforced materials as examples. However, typically implantable devices such as a screw intended to penetrate cortical bone would be made of 316L implantable grade stainless steel. As for the tubular shaft, if the diameter/perimeter of the shaft is not a limiting factor of the design, materials such as plastic may be used. Material selection may also be driven by whether the delivery system handle is disposable or reusable in order to reduce device and/or packaging costs. In one embodiment, due to tissue and bone growth, absorbable materials may be used for the fastener material, if applicable.

One of the many design purposes of the inventive fixation ring is that it not only maintains the fastener central to the fixation ring, but it may also maintain the fastener central to the tubular shaft throughout the entire process of initiation of fixation through self deployment. Similarly the fixation head facilitates the same function maintaining the heads of the fixation fastener central to the tubular shaft throughout deployment. In one embodiment, the above-described design features are a preferred part of the inventive nature of the self deploying fastener, as they maintain perfect central alignment of the drill tip during the initial start of the one-step drilling as well as during self-deployment. This perfect fastener alignment is also critical so that the fastener head remains central to the tubular shaft and connected to the slidably connected drive pin when engaged by the surgeon. In one embodiment, the slidably connected drive pin not only remains central to the handle but is also allowed to freely rotate as it moves axially in both the distal and proximal directions. The drive pin desirably has both distal and proximal ends, whereas the distal end has a mating shape adapted to engage with the fastener head and the proximal end may have various standard or custom designs to engage with a power source generating rotational motion. In one embodiment, the rotatably-slidable drive pin is captured in the system's handle and spring loaded proximally to a stop while being allowed to move distally for compressing the spring until reaching a distal stop. The length and stroke of the rotatably-slidable drive pin is of a length sufficient to allow self-deployment of the fastener and remain engaged in the fastener's head as well as having sufficient distal travel to allow the surgeon visual acuity to reconnect the distal end of the drive pin into the fastener head for adjustment or removal.

Although the intended use of tissue fastening system is to be perpendicular to the area of attachment, this may not always be possible and as such the distal features on the tubular shaft and fixation ring will aid in maintaining location at initiation. However, to further ensure positive connection between the fastener head and distal end of the drive pin, the end may have features know to allow some angular misalignment between the fastener and the drive pin.

The head of the fastener may have a variety of connection means known to those skilled in the art and aligned to tools common in the surgical theater. In one embodiment, the drive head may be small in diameter, low in profile, smooth and have an internal or recessed drive design. In one embodiment, depending upon the application, alternate head or drive designs including but not limited to the central location may be located on the outer diameter of the head having engagement drive features such as a hex. In one embodiment, the fastener head diameter/perimeter may be equal to or less than the inner diameter of the tubular shaft and it does not need to be circular or round as long as the heads may spin freely and remain central to the tubular shaft. The fixation head may have protrusions on the distal-most surface of the head to engage and/or serve as a locking means or means of controlling compressive forces on the tissue, and which is designed to flex or to cause flex or move as it comes in contact with the most proximal surface of the fixation ring. The distal protrusions on the most distal surface of the fixation head may be made of an alternative material than the fastener head and may have features that are symmetrical or randomly located throughout the head surface. Alternatively, the protrusions as described herein may be located proximally on the fixation ring's surface to achieve similar function. The distal surface of the head does not need to be in contact with the first thread, ridge or groove of the linear shaft of the fastener as shown, however, in one embodiment, it could be arranged as such.

Self-deployment is one of many creative and inventive design features of this concept, and as discussed, that is controlled by design features on both the tubular shaft and/or the fixation ring of the fixation fastener. However, surgeons need to have means of control during deployment and typically that is either visual, tactical, and audible, and/or a combination of the three. In one embodiment, one or more tubular slots on a tubular shaft provide the surgeon with visual acuity as the fastener head is moving distally down the tubular shaft.

In one embodiment, the tubular shaft may have tubular grooves that prevent rotational movement of the fixation ring during deployment through engagement with the outermost radial protrusions of the fixation ring, thus preventing any rotation or movement of the tissue being repaired. Once the radial features of the fixation ring exit the grooves of the tubular shaft, the distal protrusions of the fixation ring will desirably engage into or come in contact with the bone to further limit or prevent rotational movement of the tissue. Lengths and/or shape of the distal fixation ring protrusions may be varied depending on tissue thickness, procedures and/or design.

In one embodiment, the tubular shaft has additional features at its distal tip for use in locating or moving tissue, or providing tip security once positioned, and the length of these distal protrusions can act as yet a final visual and tactical indicator for the surgeon showing that full deployment has occurred. In one embodiment, this may be accomplished when the fastener head makes contact with the fixation ring forcing the fixation ring out of the tubular groove, which not only releases the self-deploying fastener but simultaneously releases the once securely connected tubular system from the fastener which is firmly imbedded in bone. The additional visual acuity is novel and unobvious because the fastener head can be visualized in the "V" like openings thus ensuring the surgeon of full and proper linear deployment as well as being able to assess if sufficient tissue compression or fixation has occurred before removing the insertion system.

In one embodiment, the distal tubular features on the tubular shaft may be of any shape, design angle, profile, number, sharpness, radius or distal length to either align with the fixation head, and/or tissue thickness. In one embodiment, they are preferred to be of a usable length as described but may be at minimum no shorter than the distal-most surface of the fixation ring.

Preferred dimension of the overall insertion system and components may be seen on the attached drawings but the components disclosed herein may be scaled larger or smaller depending on the intended surgical procedure requiring the use of a controlled self-deploying fixation means into bone.

In one embodiment, the handle may be of the shape shown in the attached drawings or of any shape suitable for its intended use.

Although the inventive devices and systems disclosed herein may be used to simply and quickly attach a single small piece of tissue to bone such as a muscle tendon, it is also envisioned that multiple self-deploying fasteners may be deployed to fixate larger pieces or tissue areas. When larger tissue areas such as in shoulder repair of the meniscus of the bone head need to be reattached it is very difficult to achieve a smooth or non-wrinkled connection as was created by nature. In one embodiment, the devices and systems disclosed herein enables surgeons to place numerous very small fixation devices spaced evenly or unevenly around the bone head without the need of "pre-drilling" a hole, which is typical in fixation systems currently available. Once placed, the surgeon may easily and quickly place a mattress type suture in a zig-zag pattern as shown between the repaired tissue and the spaced fixation devices, thereby allowing individualized suture tension to be applied to each tissue area and eliminating bunching or wrinkles. Once positioned appropriately, the surgeon may tighten each fixation point for permanently fixating the tissue.

This is currently done by drilling numerous through holes in different directions and passing multi-colored sutures so as to not mix up the order or of knot tying. This is difficult, time consuming and challenging to achieve a good repair even for the talented surgeon. The systems and devices disclosed herein overcome these problems.

In one embodiment, the devices, systems and methods disclosed herein may be used in conjunction with procedures that use pre-drilled holes in bone. Thus, even though many of the embodiments disclosed herein teach eliminating the need to pre-drill a hole in bone, in certain embodiments, it may be preferably to form one or more pre-drilled holes in bone for using the devices, systems and methods disclosed herein.

These and other preferred embodiments of the present invention will be described in more detail below.

BRIEF DESCRIPTION OF THE DRAWINGS

FIG. 2 shows a perspective view of an insertion tool of a bone fastener system, in accordance with one embodiment of the present invention.

FIG. 3 shows a partial cross-sectional view of the insertion tool shown in FIG. 2.

FIGS. 5A and 5B show a perspective view of a cartridge of a bone fastener system, the cartridge containing four of the bone screw and fixation plate units shown in FIGS. 1A-1E, in accordance with one embodiment of the present invention.

FIGS. 8A-8C show a method of affixing a tendon to bone using the bone screw and fixation plate shown in FIGS. 1A-1E, in accordance with one embodiment of the present invention.

FIGS. 14A-C and 14C-1 show a bone screw and a fixation plate, in accordance with one embodiment of the present invention.

FIG. 17 shows a perspective view of a bone screw, in accordance with one embodiment of the present invention.

FIG. 18 shows a perspective view of a fastener ring that is configured to mate with the bone screw of FIG. 17, in accordance with one embodiment of the present invention.

FIG. 19 shows a perspective view of a distal end of an insertion tool during deployment of the bone screw and the fixation plate shown in respective FIGS. 17 and 18, in accordance with one embodiment of the present invention.

DETAILED DESCRIPTION OF PREFERRED EMBODIMENTS

Figure 1A:
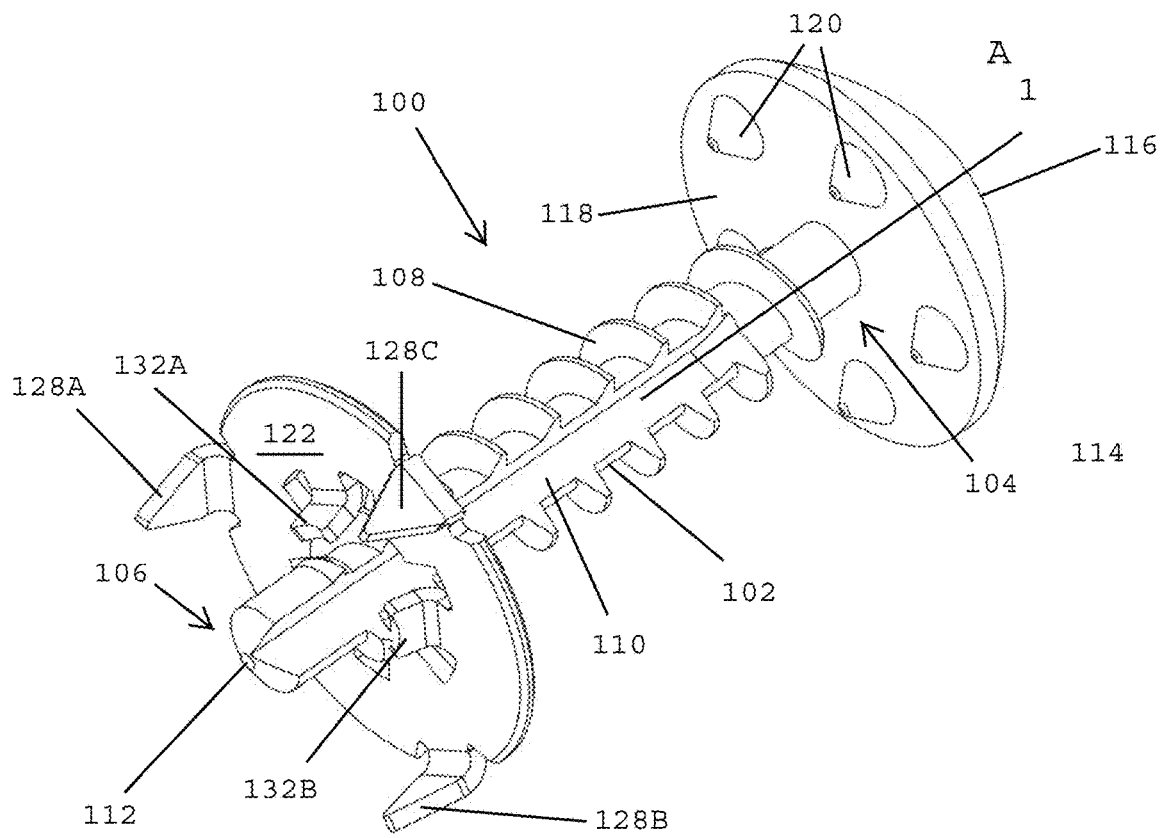
FIG. 1A shows a perspective view of a distal end of a bone fastener system including a bone screw and a fixation plate, in accordance with one embodiment of the present invention.
Figure 1B:
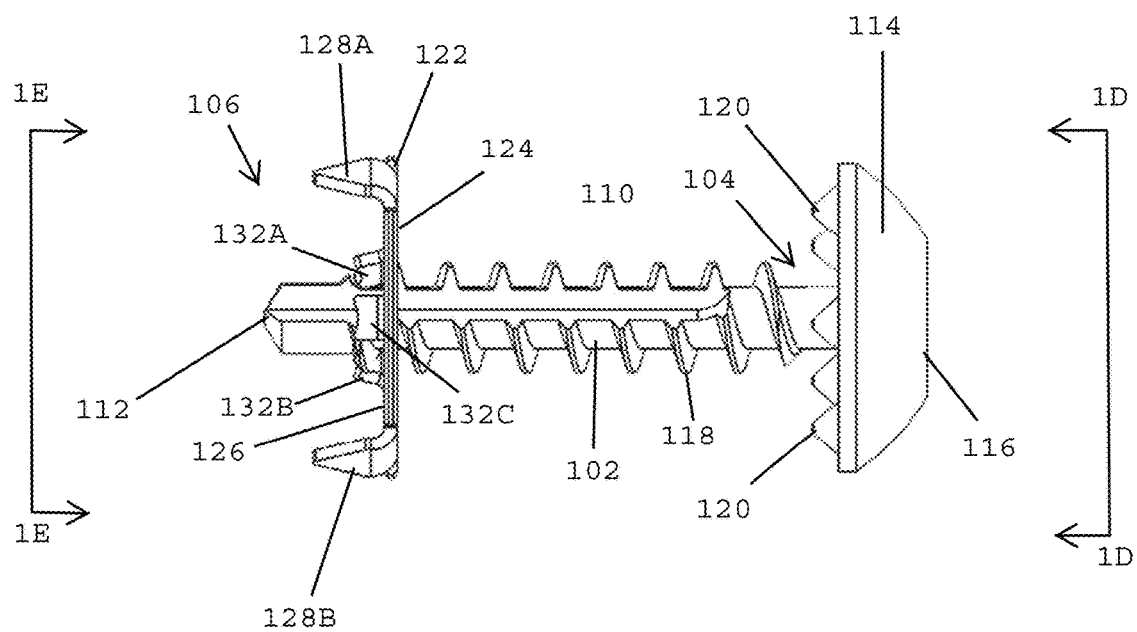
FIG. 1B shows a side view of the bone fastener system shown in FIG. 1A.
Figure 1C:
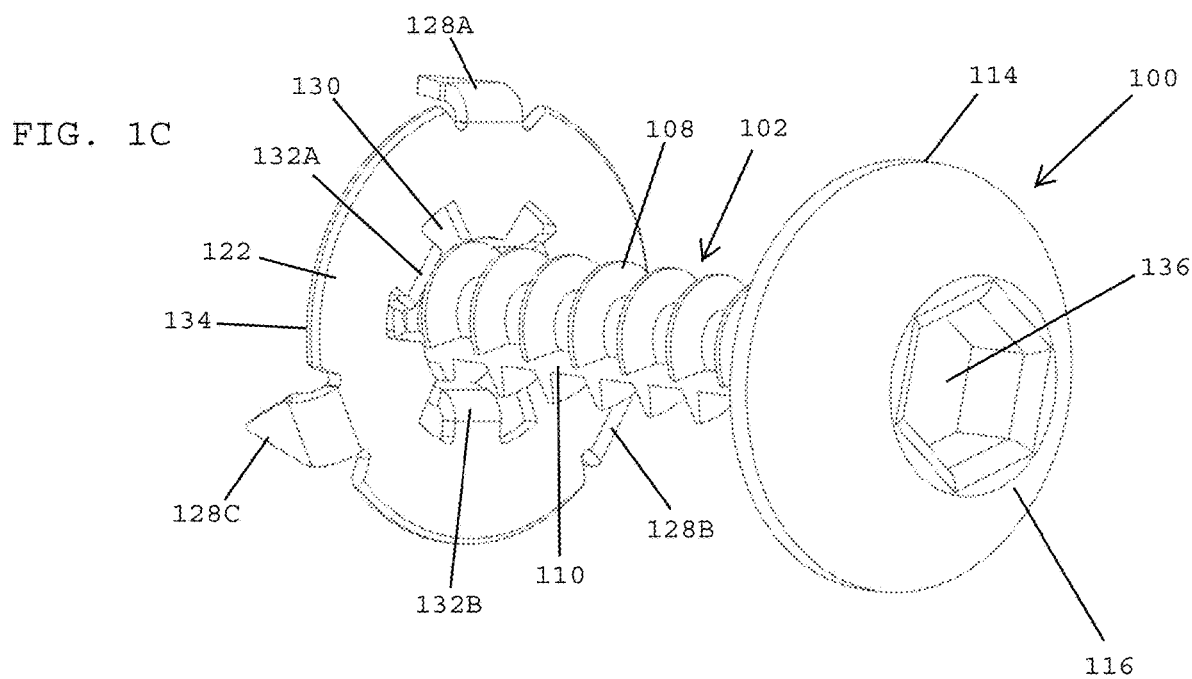
FIG. 1C shows a perspective view of a proximal end of the bone fastener system shown in FIGS. 1A and 1B.

Referring to FIGS. 1A-1C, in one embodiment, a bone fastener system preferably includes a bone screw 100 having an elongated shaft 102 with a proximal end 104, a distal end 106, and a longitudinal axis $A_1$ that extends between the proximal and distal ends 104, 106. In one embodiment, the elongated shaft 102 has helical threads 108 that extend along the length of the elongated shaft. The elongated shaft 102 preferably includes a linear void 110 that extends along the length of the elongated shaft, and that is adapted to clear bone chips created when inserting the bone screw into bone. In addition, the presence of the linear void 110 preferably reduces stress on bone as the bone screw is driven into bone and reduces the amount of force that is applied to cut hard bone, thereby minimizing trauma. In one embodiment, the distal end 106 of the elongated shaft 102 has a self-drilling tip 112 provided thereon.

In one embodiment, the bone screw 100 includes a head 114 secured to the proximal end 104 of the elongated shaft 102. The head 114 has a top side 116 and an underside 118 having a plurality of protuberances 120 spaced from one another about the underside 118 of the head 114. In one embodiment, the spaced protuberances 120 are malleable, crushable and/or deformable and may be utilized to provide a visual indicator that a sufficient locking force or torque has been attained when inserting the bone screw 100 into bone.

In one embodiment, the bone fastener system includes a fixation plate 122 that mates with the bone screw 100. In one embodiment, the fixation plate 122 desirably includes a proximal face 124, a distal face 126, and distally extending protrusions 128A-128C that project distally from the bottom or distal face 126 of the fixation plate 122. In one embodiment, the fixation plate 122 has a thickness of about 0.1-0.5 millimeters.

In one embodiment, the fixation plate 122 preferably includes a central opening 130 adapted to receive the elongated shaft 102 of the bone screw. In one embodiment, the fixation plate 122 includes spaced alignment flanges 132A-132C that are spaced from one another around the perimeter of the central opening 130 of the fixation plate 122. In one embodiment, the guide flanges 132A-132C preferably center and guide the threaded shaft of the screw in a distal direction relative to the fixation plate. In one embodiment, the guide flanges 132A-132O may also control the depth of penetration of the threaded shaft of the bone screw into bone.

Figure 1D:
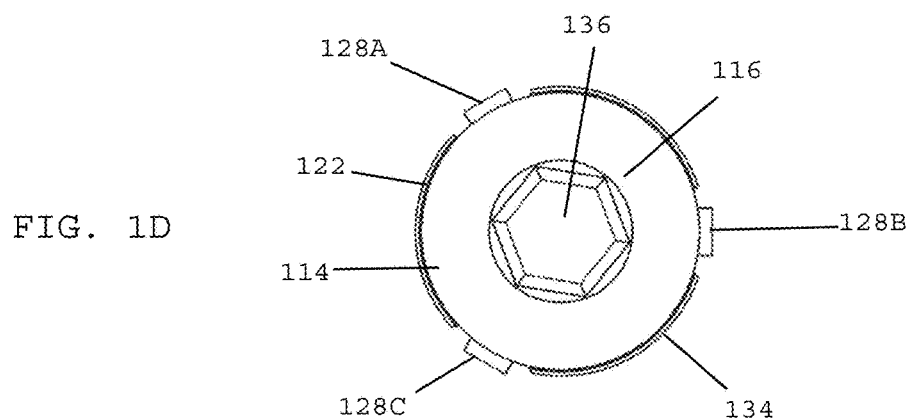
FIG. 1D shows a proximal end view of the bone fastener system shown in FIGS. 1A-1C.

Referring to FIGS. 1C and 1D, in one embodiment, the fixation plate 122 preferably has an outer perimeter edge 134 that extends around the outer perimeter of the fixation plate and between the distally ending protrusions 128A-128C. In one embodiment, the outer perimeter edge 134 functions to locate and retain the fixation plate within the cannula of an insertion tool as will be described in more detail herein. In one embodiment, the outer perimeter edge 134 may formed a releasable friction fit connections with a ring-shaped groove formed inside a cannula of an insertion tool. In one embodiment, the outer perimeter edge 134 of the fixation plate provides a self-centering and self-deploying mechanism for controlling the alignment, orientation and/or centering of the bone fastener as it moves distally through the shaft of an insertion tool.

In one embodiment, the top side 116 of the head 114 has a tool opening 136 adapted to receive a tool for rotating the head 114 of the bone screw for driving the bone screw 100 into bone. In one embodiment, the tool opening is adapted to receive a hex-shaped tool. In other embodiments, the tool opening 136 may be adapted to receive various other driving tools such as a Phillips head screwdriver, a slotted screwdriver, or a TORX driving tool.

Figure 1E:
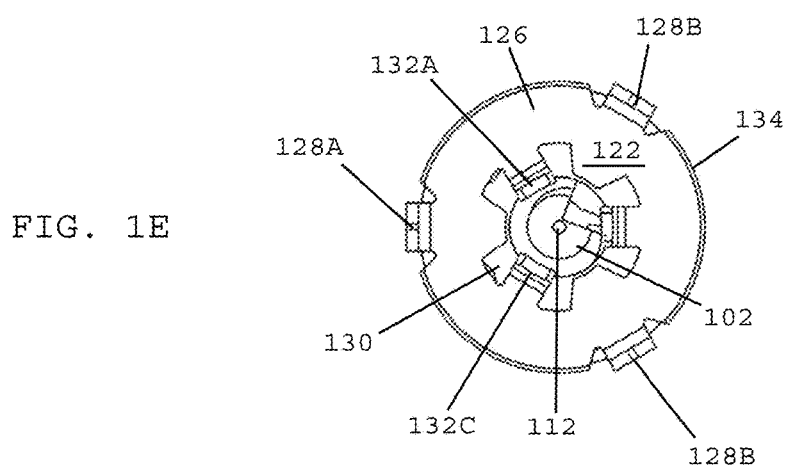
FIG. 1E shows a distal end view of the bone fastener system shown in FIGS. 1A-1C.

Referring to FIG. 1E, in one embodiment, the self-drilling tip 112 at the distal end of the elongated shaft 102 of the bone screw preferably passes through the central opening 130 of the fixation plate 122. The guide flanges 132A-132O spaced around the perimeter of the central opening 130 preferably engage the external threads on the elongated shaft 102 of the bone screw for centering and guiding the elongated shaft relative to the fixation plate 122. The distally extending protrusions 128A-128C on the fixation plate 122 desirably project distally from the distal face 126 of the fixation plate 122.

In one embodiment, the distally extending protrusions 128A-128C of the fixation plate 122 preferably have a length of about 0.5-4 millimeters. The distally extending protrusions are adapted to prevent spinning of the fixation plate relative to the tendon and/or bone engaged by the protrusions. The distally extending protrusions may also function to control the depth of insertion into bone, thereby preventing collapse of a tendon. The distally extending protrusions may also enable hard torqueing of a bone screw as it is driven into bone.

In one embodiment, the distally extending protrusions 128A-128C are designed to not penetrate into the cortical layer of bone. In one embodiment, there is no need to bend and/or wrap the distally extending protrusions around the tendon like a staple.

In one embodiment, the threaded bone screw preferably has a length of about 19-24 millimeters and an outer diameter of about 3.5-4.5 millimeters. For hand surgery, the outer diameter of the bone screw may be about 1.5-2.0 millimeters and more preferably about 1.8 millimeters.

In one embodiment, a cortical layer of bone is about 2.3 millimeters thick and the threaded screw only needs to penetrate the cortical layer to provide for proper fixation.

In one embodiment, the head 114 of the threaded fastener has an outer diameter of less than 10 millimeters and a height between the underside 118 and the top side 116 of about 0.5-2.5 millimeters.

Referring to FIG. 2, in one embodiment, a bone fastener system desirably includes an insertion tool 154 for inserting the bone screw and the fixation plate of FIGS. 1A-1E into bone. In one embodiment, the insertion tool 154 has a handle 152 provided at a proximal end 154 of the insertion tool 150 and an elongated tubular shaft 156 that extends to a distal end 158 of the insertion tool. In one embodiment, the tubular shaft 156 may be made of biocompatible material such as metal or plastic. In one embodiment, the handle 152 may be made of plastic and may have an outer surface with knurling 160 for securely grasping the insertion tool.

In one embodiment, the tubular shaft 156 includes a proximal shaft section 162 and a distal shaft section 164. In one embodiment, the proximal shaft section 162 has a length of about 7-9 centimeters and a diameter of about 5.5-8.25 millimeters, and the distal shaft section 164 has a length of about 5-6 centimeters and an outer diameter that is smaller than the outer diameter of the proximal shaft section 162 of the tubular shaft 156. The distal shaft section 164 of the tubular shaft 156 preferably includes elongated slots 166 that are open at the distal-most end of the tubular shaft 156. The elongated slots 166 are desirably spaced from one another around the perimeter of the distal shaft section 164 and are adapted to receive the distally extending projections 128A-1280 on the fixation plate 122 (FIGS. 1A and 1D).

In one embodiment, the insertion tool 150 desirably includes a driver bit 168 that is accessible at the proximal end 154 of the tool. In one embodiment, the driver 168 may be pre-loaded with a socket drive tip and handed to a surgeon with a bone screw and fixation plate pre-loaded into the insertion tool.

Referring to FIG. 3, in one embodiment, an insertion tool 150' desirably includes a spring 170' that is coupled with the driver bit 168'. In one embodiment, the spring 170' serves to keep the driver bit 168' under tension or compression for control during attachment of a power driver to the driver bit 168'. In addition, the spring 170' desirably minimizes disengagement between the proximal end of the driver bit 168' and a power driver during a surgical procedure for anchoring a bone screw into bone.

Figure 4A:
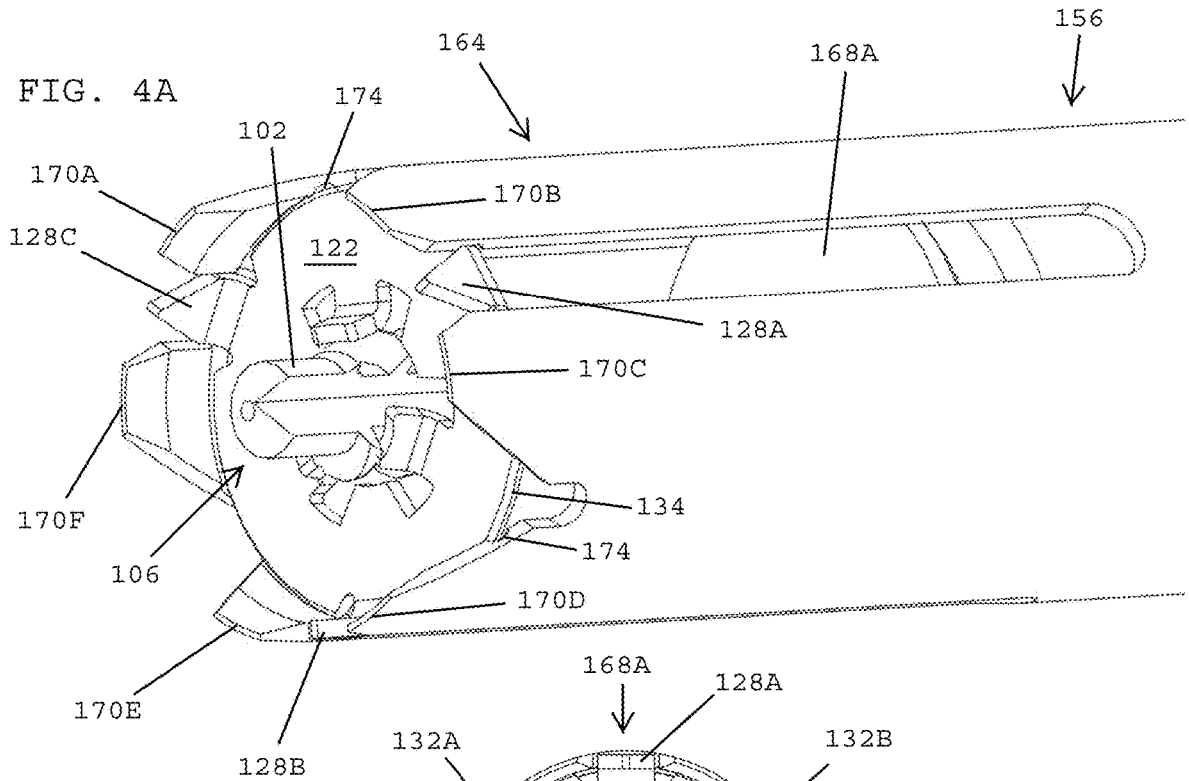
FIGS. 4A-4C show the bone screw and fixation plate of FIGS. 1A-1E disposed within the distal end of the insertion tool shown in FIG. 2, in accordance with one embodiment of the present invention.
Figure 4B:
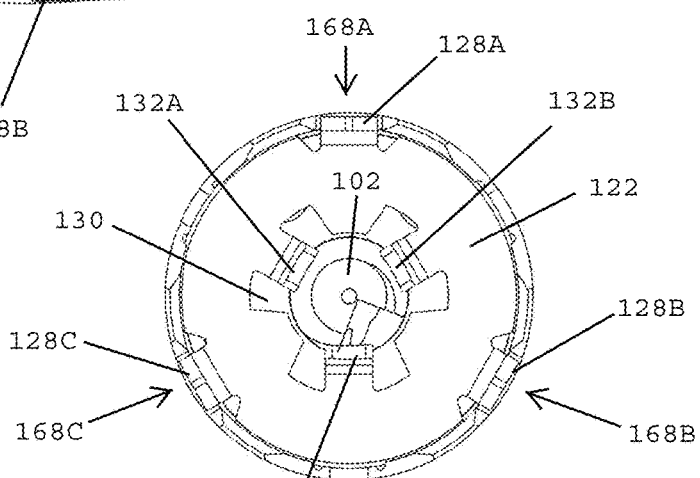

Referring to FIGS. 4A and 4B, in one embodiment, the distal shaft section 164 of the tubular shaft desirably includes three elongated slots 168A-168C that are spaced from one another around the open perimeter of the tubular shaft and that are open at the distal most end of the tubular shaft 156 (FIG. 2). In one embodiment, the distally extending protrusions 128A-128C of the fixation plate 122 are disposed within the respective elongated slots 168A-168C of the distal shaft section 164, which prevents the fixation plate 122 from spinning as the distal end 106 of the threaded shaft 102 is advanced into bone. The guide flanges 132A-132C around the central opening 130 of the fixation plate 122 preferably align, orient, guide and/or center the elongated shaft 102 of the bone screw as it moves distally relative to the fixation plate 122 and the distal end of the insertion tool.

Referring to FIG. 4A, in one embodiment, the distal-most end of the distal shaft section 164 of the tubular shaft 156 preferably has castling 170A-170F or teeth that are pressed against a tendon and/or bone for providing stability at the distal end of the tubular shaft 156 as the bone screw is deployed.

In one embodiment, the elongated slots 168A-1680 preferably extend along the longitudinal axis of the tubular shaft 156 and provide visualization of the bone screw and the fixation plate 122 as the components move distally through the tubular shaft 156.

Figure 4C:
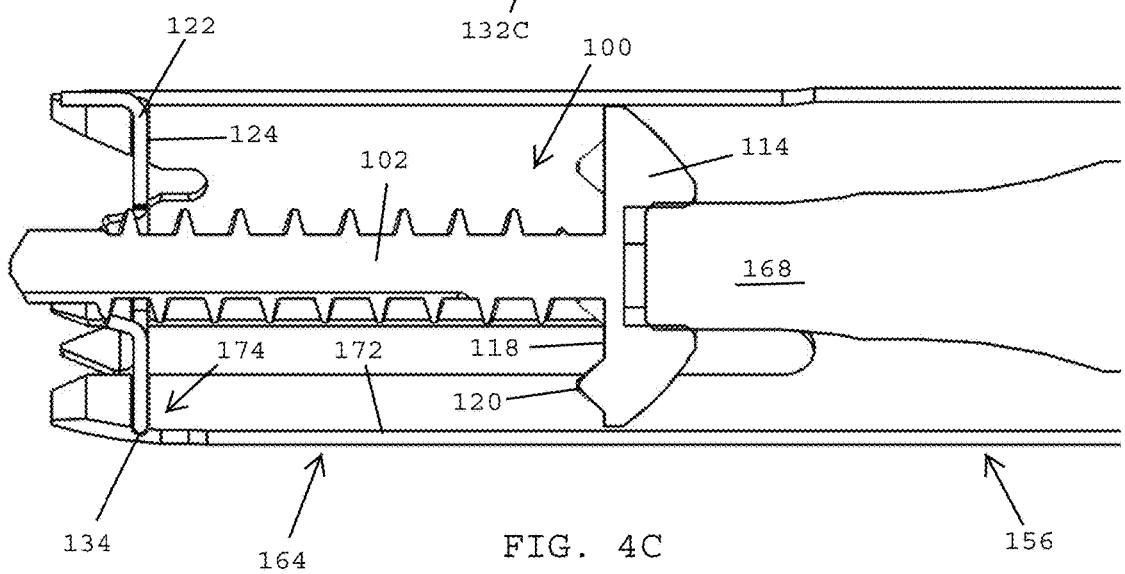

Referring to FIG. 4C, in one embodiment, the distal shaft section 156 of the tubular shaft 164 has an inner diameter that is slightly larger than the outer diameter of the head 114 of the bone screw 100. The close tolerance between the outer diameter of the head 114 and the inner diameter of the distal shaft section 156 provides a self-centering and alignment system as the threaded bone screw moves distally through the tubular-shaped shaft 156.

In one embodiment, the distal shaft section 164 of the tubular shaft 156 has an inner surface 174 including a ring-shaped groove or depression 174 formed in the inner surface that is adapted to receive the outer peripheral edge 134 of the fixation plate 122. In one embodiment, the ring-shaped depression 174 formed in the inner surface 172 of the distal shaft section 164 holds the fixation plate 122 in place at the distal end of the tubular shaft until the underside 118 of the head 114 of the bone screw engages the proximal face 124 of the fixation plate 122, at which point the head may decouple the fixation plate from being secured to the end of the tubular shaft. In one embodiment, the ring-shaped depression 174 is a retention feature for retaining the fixation plate 122 inside the tubular shaft of the insertion tool until the underside of the head 114 (e.g., the protuberances 120 in FIG. 1A) decouples the fixation plate 122 from its initial connection with the distal end of the tubular shaft.

Referring to FIG. 5A, in one embodiment, a bone fastener system may include a cartridge 180 that contains a plurality of bone screw and fixation plate units secured therein. The cartridge 180 desirably includes a proximal end 182 that seats the head 114 of the bone screw and a distal end 184 that seats the fixation plate 122. In one embodiment, the proximal end 182 of the cartridge 180 preferably includes alignment projections 186A-186C that are adapted to engage the elongated slots 168A-168C of the tubular shaft of the insertion tool, and distal end 184 of the cartridge 180 includes one or more alignment depressions 188 formed therein that are adapted to engage the distally extending projections 128 on the fixation plate 122 for insuring proper alignment of the tubular shaft of the insertion tool with the bone fastener and the distally extending protrusions 128 of the fixation plate 122.

In one embodiment, the alignment projections 186A-186C located at the proximal end 182 of the cartridge 180 are in axial alignment with alignment depressions 188 located at the distal end 184 of the cartridge 180.

Referring to FIG. 5B, in one embodiment, the elongated slots 168A-168C of the distal shaft section 164 of the tubular shaft 156 slide over the alignment projections 186A-186C of the cartridge 180 for guiding the elongated slots 168A-168C into alignment with the distally extending protrusions on the fixation plate 122.

Figure 6A:
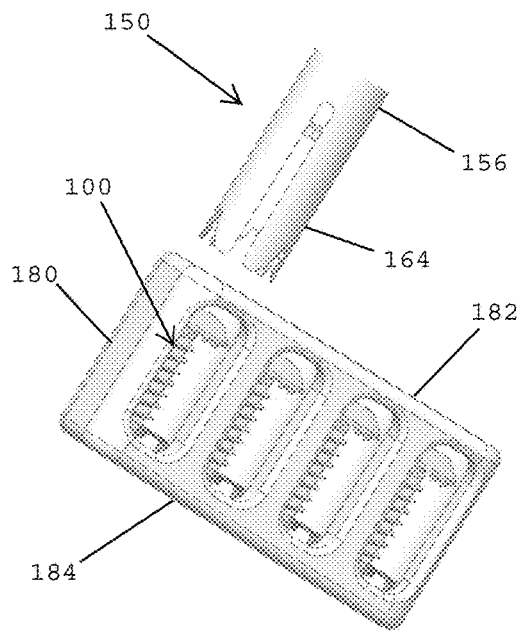
FIGS. 6A-6D show a method of removing a bone screw and fixation plate unit from a cartridge, in accordance with one embodiment of the present invention.

Referring to FIG. 6A, in one embodiment, the distal end of the insertion tool 150 is desirably inserted into an opening at the proximal end 182 of the cartridge 180 to load a bone screw 100 with a fixation plate onto the distal shaft section 164 of a tubular shaft 156.

Figure 6B:
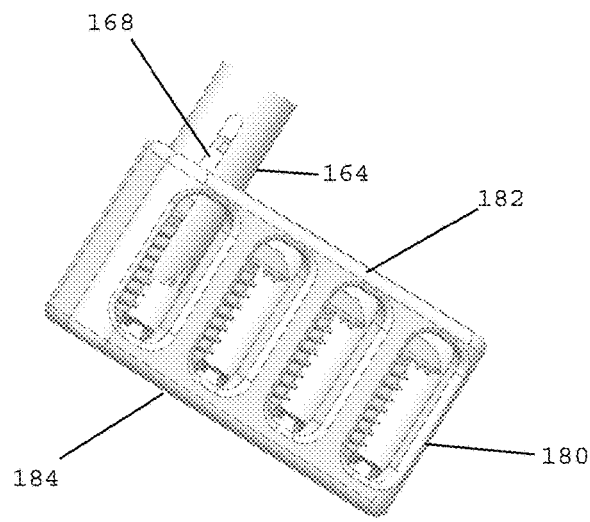
Figure 6C:
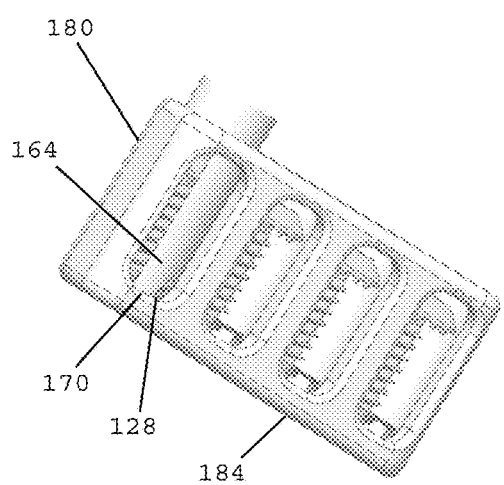

Referring to FIG. 6B, in one embodiment, the elongated slots 168 on the distal shaft section 164 of the tubular-shaped shaft are aligned with the alignment projections 186 (FIG. 5B) at the proximal end 182 of the cartridge 180. The distal shaft section 164 is advanced toward the distal end 184 of the cartridge. The distal shaft section 164 of the tubular-shaped shaft is extended distally until the castling 170 at the distal-most end of the distal section 164 abuts against a floor at the distal end 184 of the cartridge 180. At this stage, the distally extending protrusions 128 on the fixation plate are disposed within the elongated slots 168 (FIG. 6B). The outer perimeter of the fixation plate preferably forms a snap-fit or friction fit connection with the ring-shaped depression 174 (FIG. 4C) provided on the inner surface of the distal shaft section 164 of the tube-shaped shaft. The tube-shaped shaft 156 including the distal shaft section 164 thereof may be withdrawn from the proximal end 182 of the cartridge 180. At this stage, the distally extending protrusions 128A-128C are preferably disposed within the respective elongated slots 168A-168O of the distal shaft section 164 of the tubular shaft 156. The outer perimeter edge of the fixation plate is desirably secured within the ring-shaped depression 174 formed on the inner surface of the distal shaft section 164 (FIG. 4C).

Figure 6D:
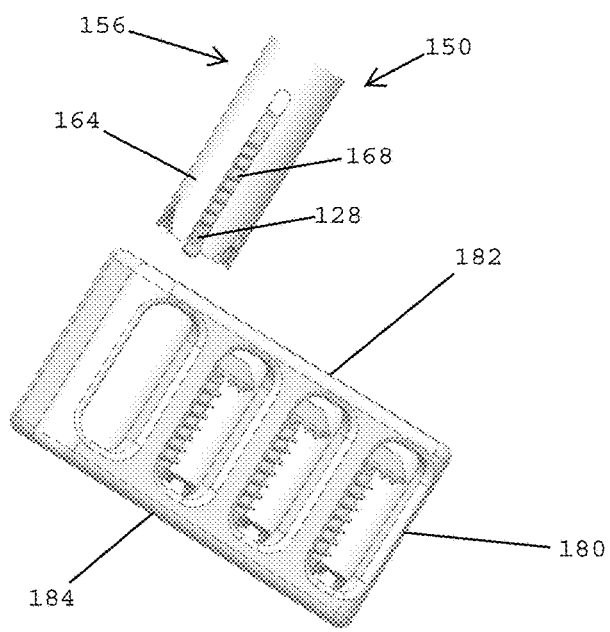
Figure 7A:
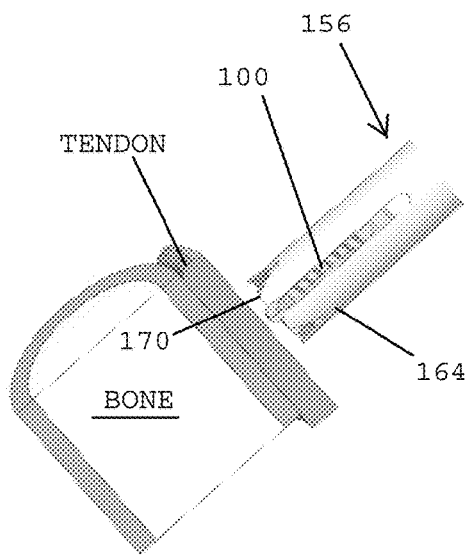
FIGS. 7A-7E show a method of using the insertion tool of FIG. 2 for affixing the bone screw and fixation plate of FIGS. 1A-1E to bone, in accordance with one embodiment of the present invention.

FIGS. 7A-7E show a method of using the pre-loaded insertion tool 150 (FIG. 6D) for fixing a tendon to a bone, in accordance with one embodiment of the present invention. Referring to FIG. 7A, in one embodiment, a bone screw and fixation plate unit is pre-loaded inside a distal shaft section 164 of a tubular shaft 156 of an insertion tool 150 (FIG. 2). With a tendon positioned over bone, the castling 170 located at the distal-most end of the tubular shaft 156 is juxtaposed with the tendon.

Figure 7B:
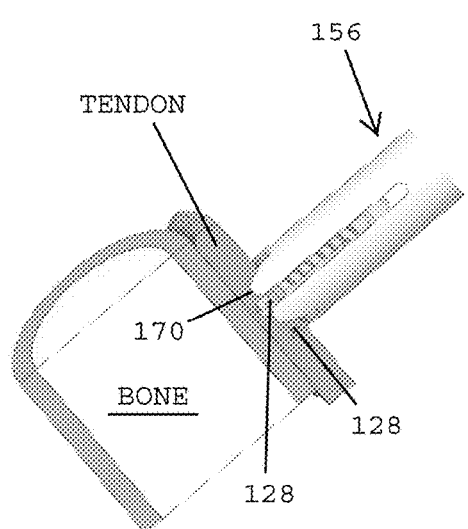

Referring to FIG. 7B, in one embodiment, the castling 170 at the distal-most end of the tubular shaft 156 is abutted against the tendon to press the tendon against the bone. The distally extending protrusions 128 on the fixation plate 122 (FIG. 4C) may also engage the tendon and/or the bone.

Figure 7C:
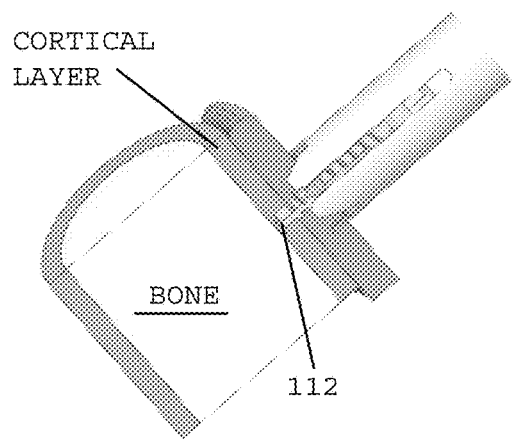

Referring to FIG. 7C, the threaded fastener is at least partially deployed (e.g., driven into bone) whereupon the self-drilling tip 112 begins to cut into the cortical layer of the bone. In one embodiment, the threaded shaft of the bone screw 100 (FIG. 1A) is rotated in a clockwise direction for advancing the self-drilling tip 112 into the cortical layer of the bone.

Figure 7D:
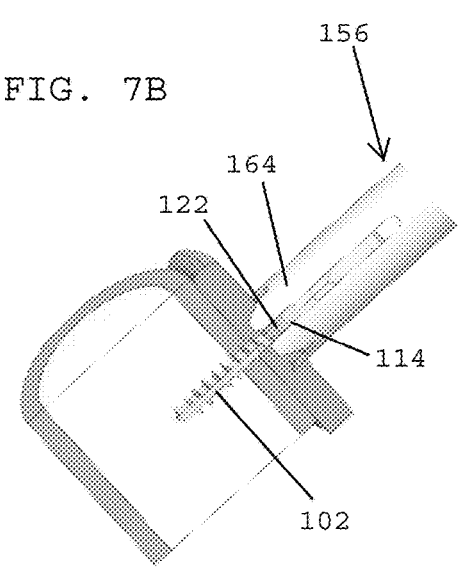

Referring to FIG. 7D, the elongated shaft 102 of the threaded fastener is further advanced into bone. The fixation plate 122 is still engaged with the ring-shaped depression formed on the inner surface of the distal section 164 of the tubular shaft 156. The surgeon can visualize the position of the head 114 of the bone screw relative to the fixation plate 122 and the distal end of the tubular shaft.

Figure 7E:
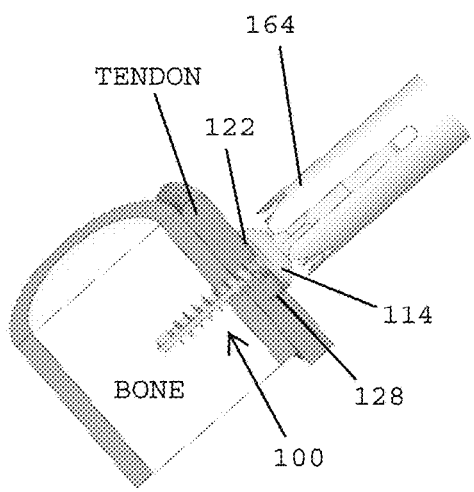

Referring to FIG. 7E, in one embodiment, as the threaded fastener is further tightened, the underside of the head 114 decouples the outer perimeter edge of the fixation plate 122 from the ring-shaped depression formed on the inner surface of the distal shaft section 164 of the tubular shaft 156 to deploy the threaded fastener and a fixation plate from the distal section 164. The distally extending protrusions 128 of the fixation plate 122 may bite into the tendon and/or the bone. The bone screw 100 and the fixation plate 122 desirably affix the tendon to the bone.

Referring to FIG. 8A, in one embodiment, a bone fastener system including a bone screw 100 and a fixation plate 122 is utilized for affixing a tendon to bone. In one embodiment, the bone fastener system includes a threaded bone screw 100 and a fixation plate 122 that is coupled with the bone screw. The fixation plate 122 preferably includes one or more distally extending protrusions 128 that engage the tendon and/or the bone.

FIG. 8B shows four bone screws 100A-100D being utilized for fixing a tendon to bone. Each of the bone screws 100A-100D mates with a fixation plate 122 having distally extending protrusions 128 that engage the tendon and/or the bone. The distal-most ends of the distally extending protrusions preferably do not contact the bone surface. The bone screws 100A-100D include a head 114 that may be engaged by a tool for driving a threaded shaft of bone screw through the tendon and into the bone. In one embodiment, the bone screw is tightened until an underside of the head 114 engages a top side or proximal face of the fixation plate 122.

Referring to FIG. 8C, in one embodiment, after the bone screws 100A-100D are anchored in the bone, a suture material 190 may be utilized for interconnecting the anchored bone screws 100A-100D for improving the stability of the fixation of the tendon to the bone.

Figure 9A:
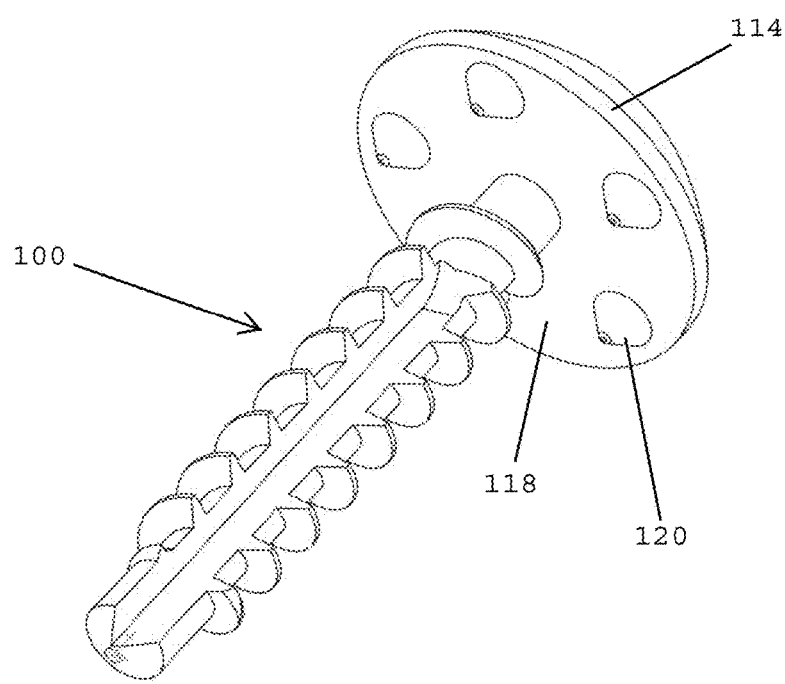
FIGS. 9A-9C show a method of monitoring the amount of torque applied to a bone screw, in accordance with one embodiment of the present invention.

Referring to FIG. 9A, in one embodiment, a bone screw 100 desirably includes a head 114 having an underside 118 and spaced malleable, crushable and/or deformable protuberances 120 projecting from the underside 118 of the head 114.

Figure 9B:
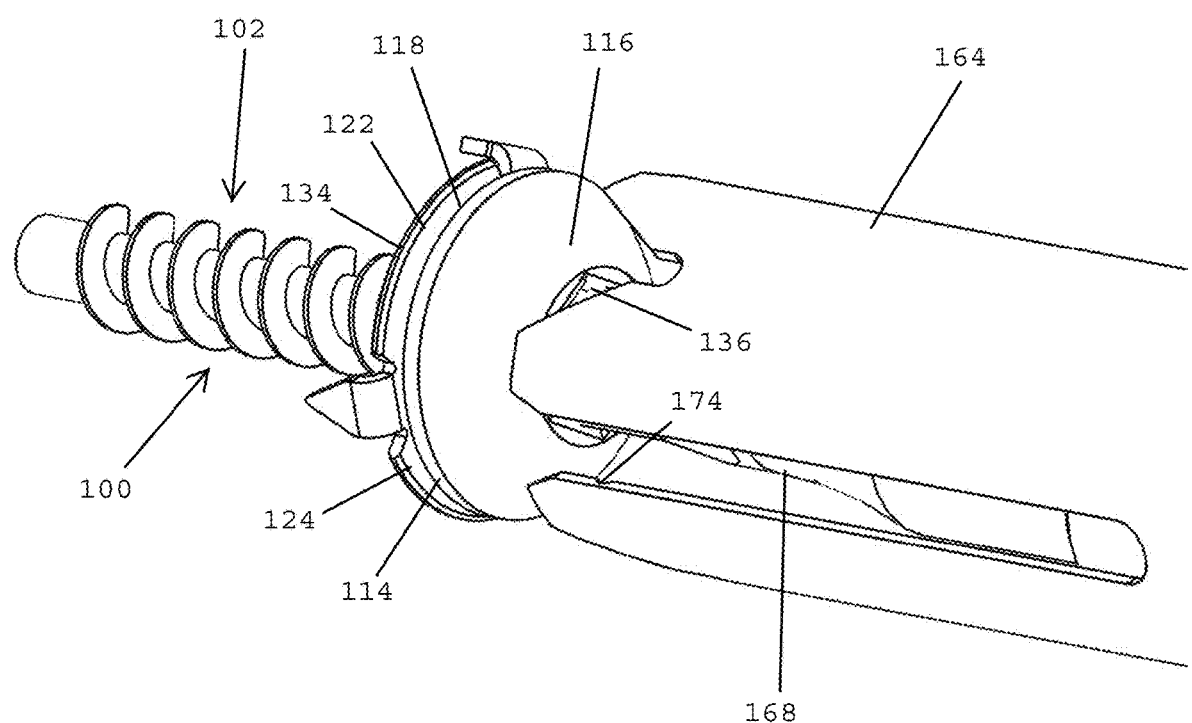

Referring to FIG. 9B, in one embodiment, a distal end of a bone screw driver 168 engages a tool opening 136 formed in the top side 116 of the head 114 of the bone screw for driving the threaded elongated shaft 102 of the bone screw into bone. As the bone screw is advanced in a distal direction, the underside 118 of the head 114 engages the proximal face 124 of the fastener ring 122 for decoupling the outer perimeter edge 134 of the fixation plate 122 from the ring-shaped groove 174 provided inside the distal shaft section 164 of the tubular shaft of the insertion tool.

Figure 9C:
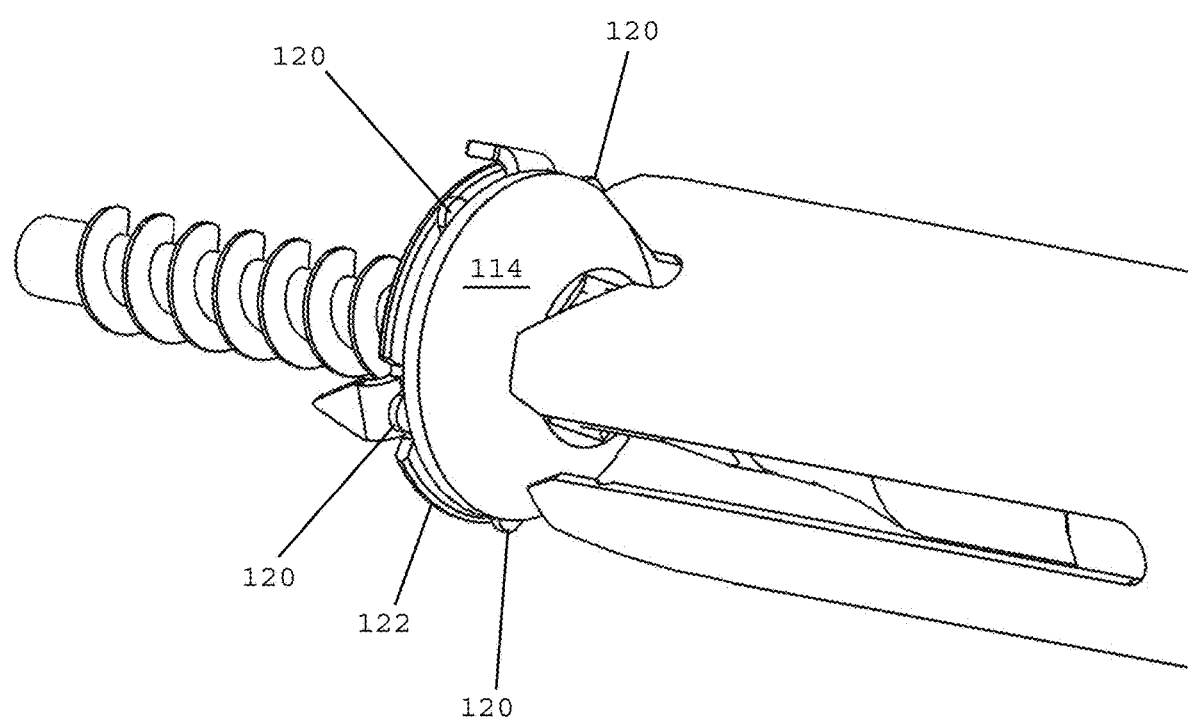

In FIG. 9B, the protuberances 120 projecting from the underside of the head of the bone screw (FIG. 9A) are not yet visible because the bone screw has not yet been tightened down to a desired torque relative to the fixation plate 122. In FIG. 9C, when the bone screw 100 has been tightened to a desired torque relative to the fixation plate 122, the malleable protuberances 120 (FIG. 9A) on the underside of the head 114 become deformed so as to be visible to a surgeon for indicating that a desired torque level has been attained.

Figure 10A:
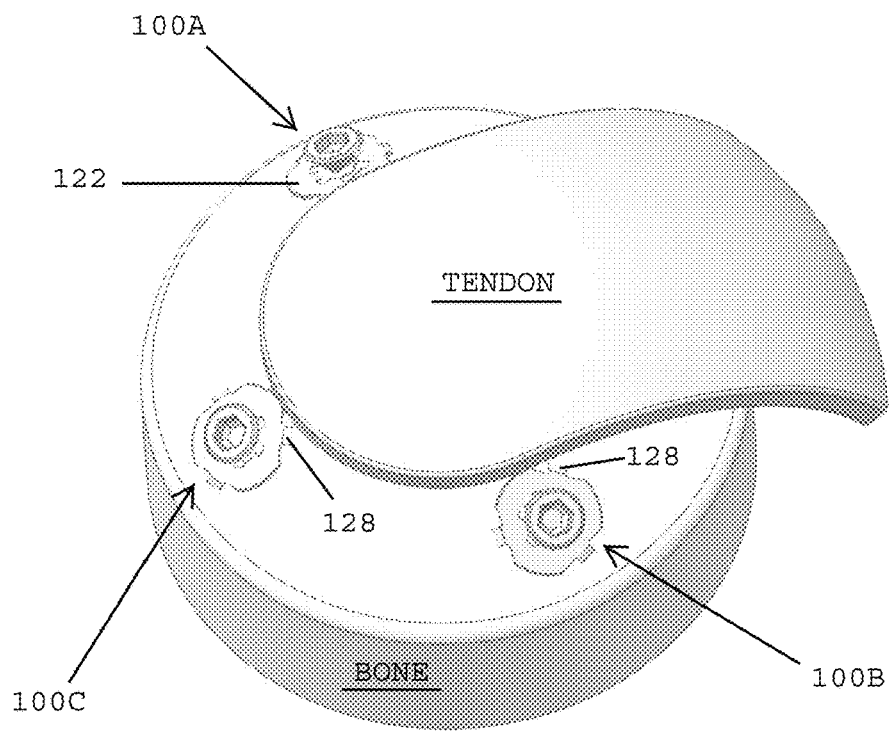
FIGS. 10A-10B show a method of securing a tendon to bone using the bone screw and fixation plate shown in FIGS. 1A-1E, in accordance with one embodiment of the present invention.
Figure 10B:
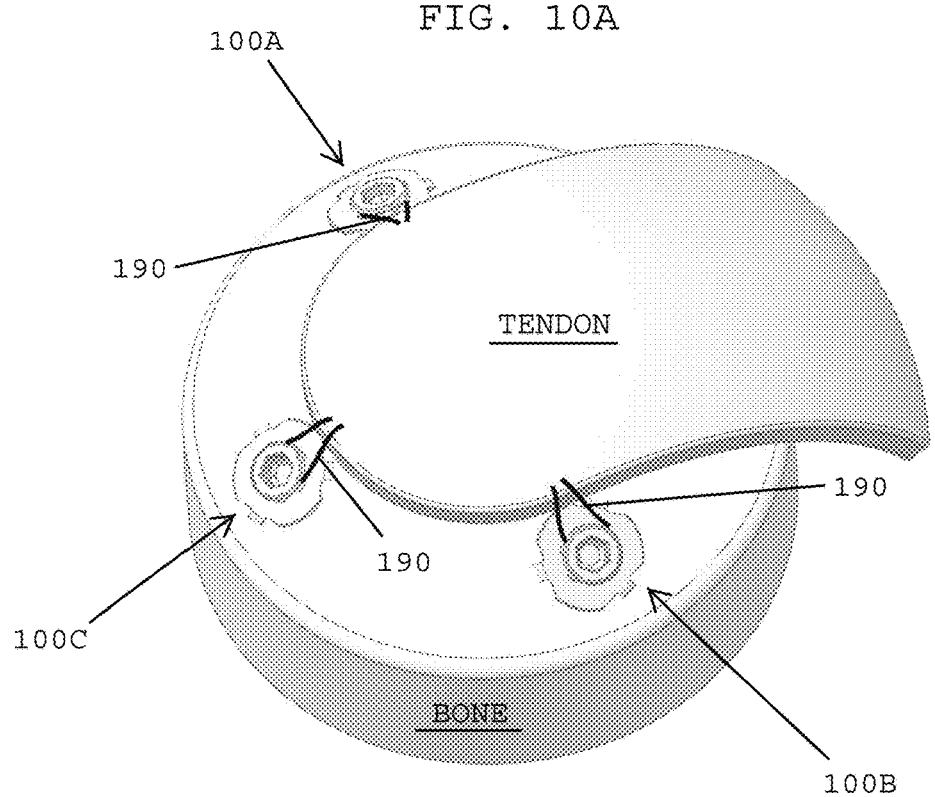

FIGS. 10A and 10B show another method of fixing a tendon to bone. Referring to FIG. 10A, in one embodiment, three bone screws 100A-100C similar to those described above are anchored into bone. Each bone screw is preferably coupled with a fixation plate 122 having distally extending protrusions 128 that extend distally from a bottom or distal face of the fixation plate. In one embodiment, the distally extending protrusions 128 desirably engage the bone.

Referring to FIGS. 10A and 10B, in one embodiment, after the bone screws 100A-110C are anchored in the bone, a tendon is positioned atop a bone, and suture material 190 is utilized for fixing the tendon to the anchored bone fixation systems 100A-100C, which insures that the tendon is fixated to the bone.

Figures 11, 12:
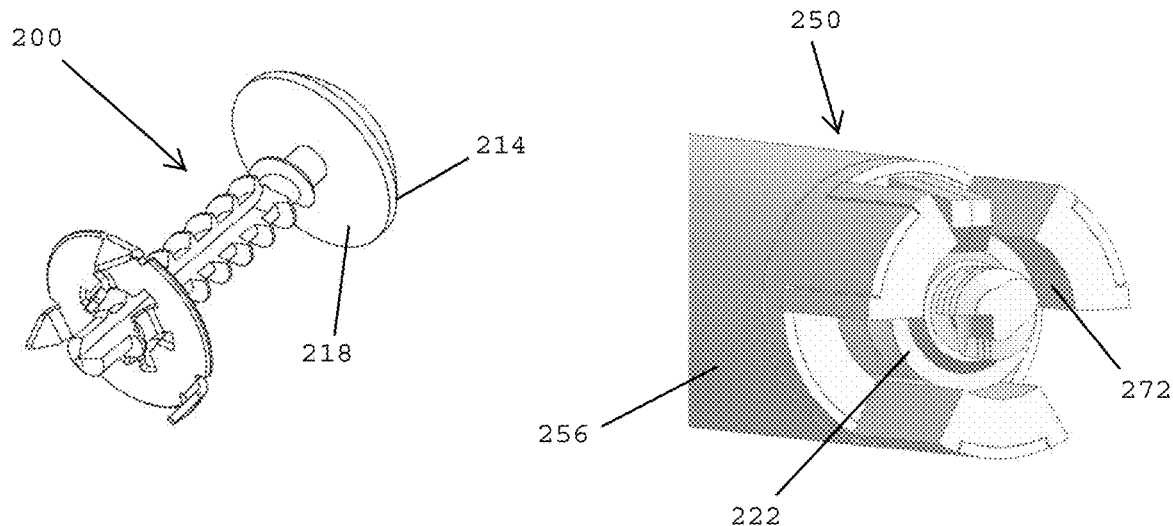
FIG. 11 shows a perspective view of a distal end of a bone screw and a fixation plate, in accordance with one embodiment of the present invention.
FIG. 12 shows a perspective view of a distal end of an insertion tool having a pro-loaded bone screw and fixation plate, in accordance with one embodiment of the present invention.

Referring to FIG. 11, in one embodiment, a bone fastener system preferably includes a bone screw 200 having a head 214 with an underside 218. The underside 218 of the head 214 does not include deformable or compressible protuberances as described above in the embodiment shown in FIGS. 9A-9C.

Referring to FIG. 12, in one embodiment, an insertion tool 250 has a tubular shaft 256 that is molded or cast. The tubular shaft 256 has an inner diameter 272 that may be sized to act as a guide for a bone screw with a smaller head diameter than the outer diameter of the fixation plate 222. The inner diameter 272 desirably guides a smaller screw head while capturing the screw head and allowing for visualization of the screw.

Figure 13:
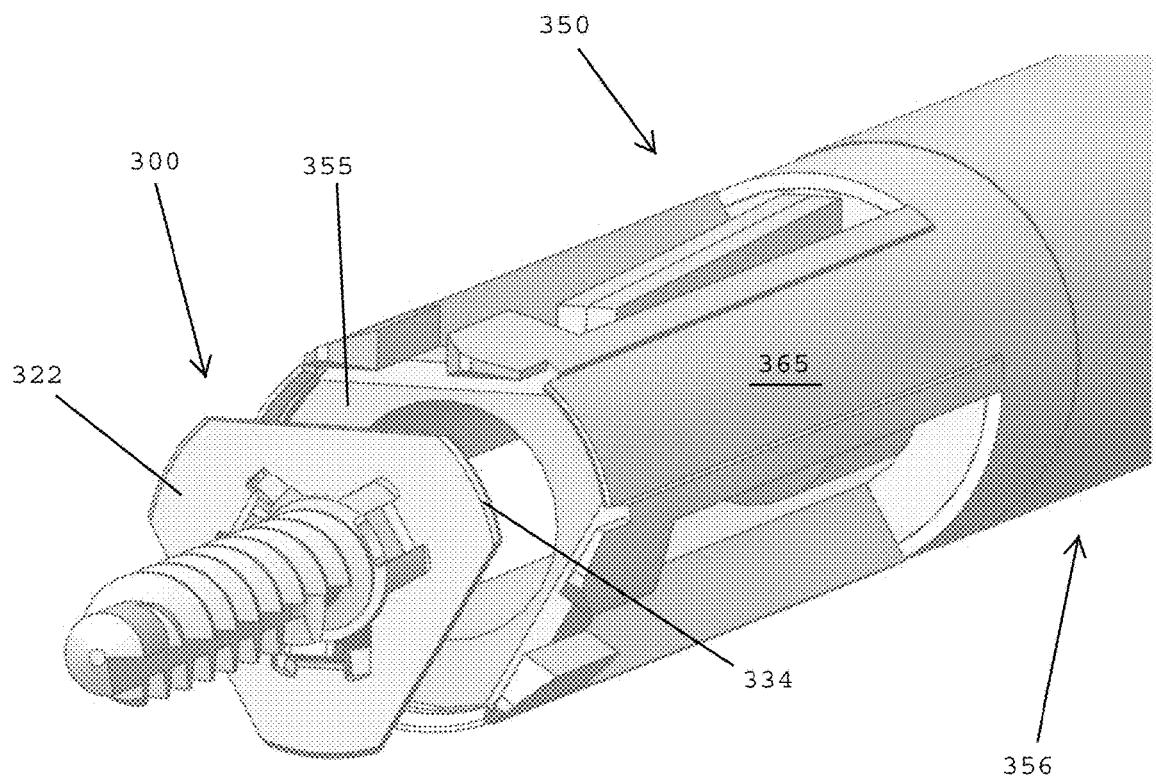
FIG. 13 shows a perspective view of a distal end of an insertion tool having a pre-loaded bone screw and fixation plate, in accordance with one embodiment of the present invention.

Referring to FIG. 13, in one embodiment, a bone fastener system may include a fixation plate 322 that is shaped to locate into a corresponding shape 355 provided at the distal end of an elongated shaft 356 of an insertion tool 350. The distal feature 355 may be part of a molded or cast tubular body and not incorporated into a retention groove function. In one embodiment, the retention grooves that engage the outer peripheral edge 334 of the fixation plate 322 may be part of a separate component 365 that is suited to retention control and sized to allow release of the fixation plate at a particular torque level applied by the head of a bone screw.

Referring to FIGS. 14A-14C, in one embodiment, a bone fastener system desirably includes a bone screw 400 having an elongated shaft 402 with external threads 408. The bone screw preferably includes a low profile head 414 provided at a proximal end 404 of the elongated shaft 402. The low profile head 414 includes a tool opening 436 adapted to receive a driving tool. The bone fastener system includes a fixation plate 422 having a central opening 430 with guide flanges 432 adapted to engage the helical threads 408 extending along the longitudinal shaft 402 of the bone screw 400. The fixation plate 422 includes distally extending protrusions 428A-428C that extend distally beyond a distal face 426 of the fixation plate 422. In one embodiment, the fixation plate 422 includes an outer peripheral edge 434 that is adapted to engage a retention ring or ring-shaped depression formed in an inner surface of tube-shaped shaft of an insertion tool.

FIGS. 14C and 14C-1 show the bone screw 400 advanced to a distal-most position relative to the fixation plate 422 so that an underside of the head 414 of the bone screw engages a peripheral face 424 of the fixation plate 422.

Figure 15A:
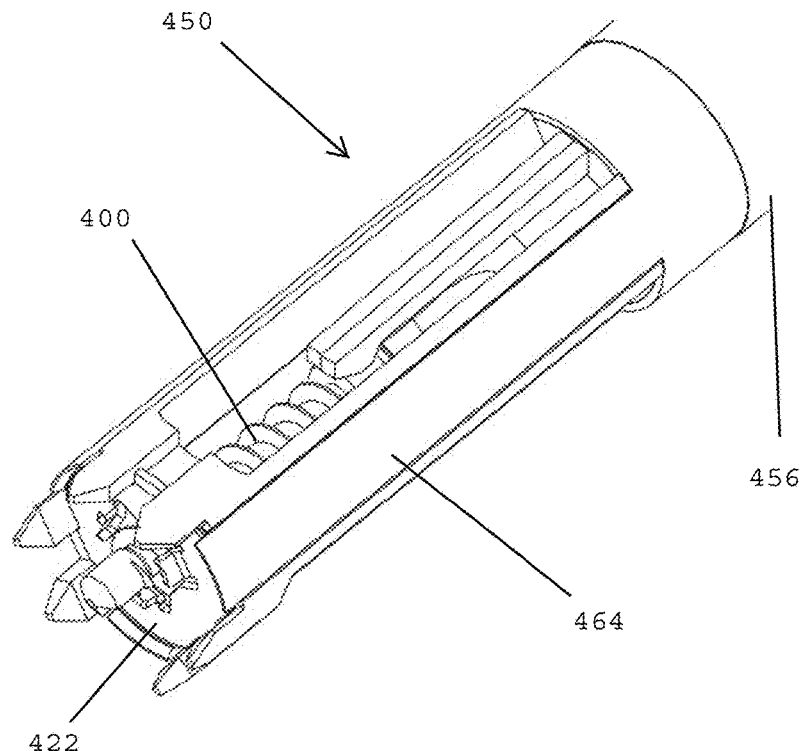
FIG. 15A shows a perspective view of a distal end of an insertion tool with the bone screw and the fixation plate of FIGS. 14A-C and 14C-1 pre-loaded into the insertion tool, in accordance with one embodiment of the present invention.
Figure 15B:
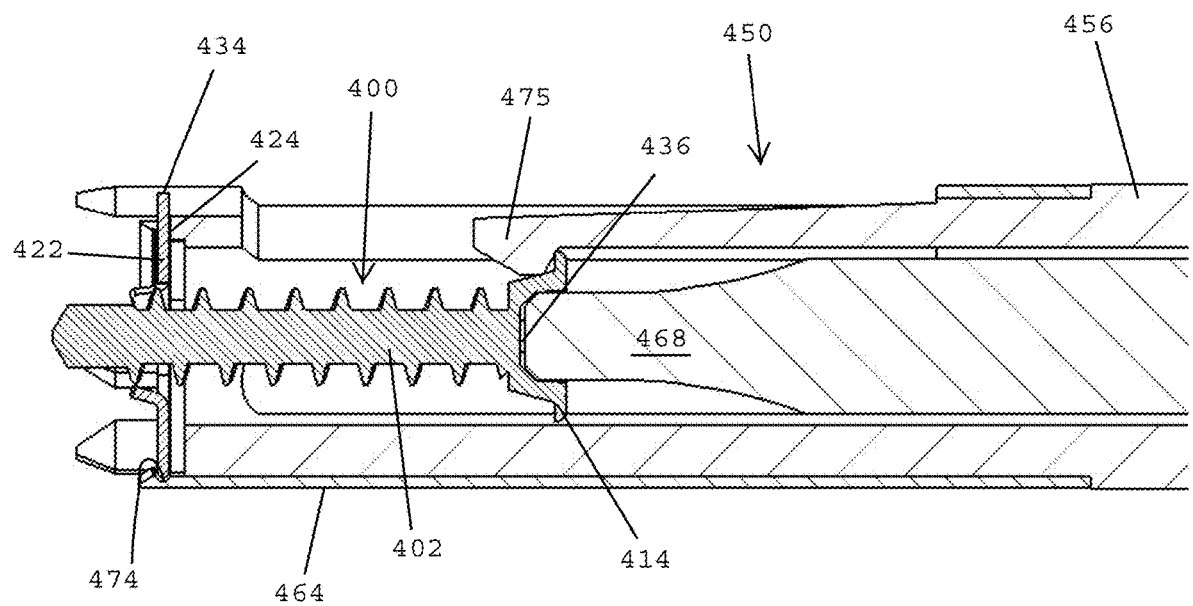
FIG. 15B shows a cross-sectional view of the insertion tool and the pre-loaded bone screw and fixation plate shown in FIG. 15A.

FIGS. 15A and 15B show the bone screw 400 and fixation plate 422 of FIGS. 14A-14C loaded into the distal end of an insertion tool 450. The fixation plate 422 is disposed adjacent the distal end of the distal shaft section 464 of the tubular shaft 456. The outer peripheral edge 434 of the fixation plate 422 is seated within a retention ring, depression or groove 474 formed in the inner surface of the distal shaft section 464 of the tubular shaft 456. The low profile head 414 of the bone screw 400 is engaged by a retention finger 475 that preferably centers, aligns, and provides guidance for the bone fastener system 440 as it is disposed within the distal section 464 of the tubular shaft 456 of the insertion device 450. The retention finger may be flexible and have spring-like characteristics. A distal end of a driver 468 engages the tool opening 436 formed in the head 414. The driver 468 is preferably rotated in a clockwise direction for advancing the elongated shaft 402 distally until the underside of the head 414 engages the proximal face 424 of the fixation plate 422.

In one embodiment, the retention finger 475 is flexible so that it may flex outwardly to enable the head 414 of the threaded fastener to move distally beyond the retention finger 475.

Figure 16:
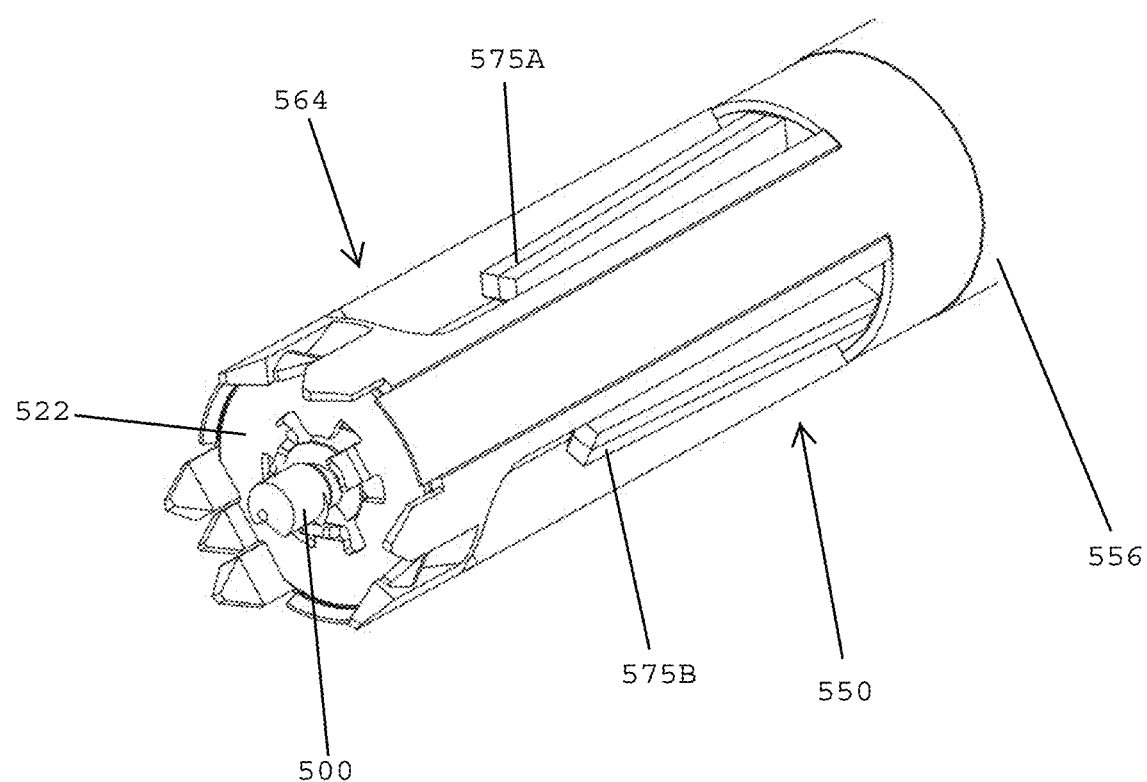
FIG. 16 shows a perspective view of a distal end of an insertion tool having a pre-loaded bone screw and fixation plate, in accordance with one embodiment of the present invention.

FIG. 16 shows an insertion tool 550 having a distal section 564 of a tubular shaft 556. The distal section 564 preferably includes a pair of retention fingers 575A, 575B that engage the head of the bone screw 500 for aligning and stabilizing the bone screw and the fixation plate 522 prior to deployment from the distal end of the insertion tool 550.

Referring to FIG. 17, in one embodiment, a bone fastener system desirably includes a bone screw 600 having a head 614 with an underside 618 having tapered or ramp-shaped protuberances 620 spaced around the underside 618 of the head 614.

Referring to FIG. 18, in one embodiment, the threaded fastener shown in FIG. 17 is adapted to mate with the fixation plate 622 shown in FIG. 18. The fixation plate 622, which has many if not all the features described above, desirably includes spaced slots or holes 625 that are adapted to receive the tapered or ramp-shaped protuberances 620 provided at the underside 618 of the head 614 of the bone screw 600 (FIG. 17) when sufficient torque has been applied to the bone screw.

FIG. 19 shows the tapered or ramp-shaped protuberances 620 of the bone screw mating with the slots or holes 625 of the fixation plate 622 after sufficient torque has been applied to the bone screw 600.

The tapered protuberances or ramp-shaped protuberances 620 preferably mate with the slots or holes 625 to provide an indication that the head 614 of the bone screw 600 has been tightened down to a sufficient level. The mating of the tapered protuberances 620 with the slots 625 may provide a tactile feedback and/or audible click to indicate sufficient tightening of the bone screw. In addition, the mating of the tapered protuberances 620 with the slots 625 may prevent loosening of the bone screw relative to the fixation plate 622.

Figure 20:
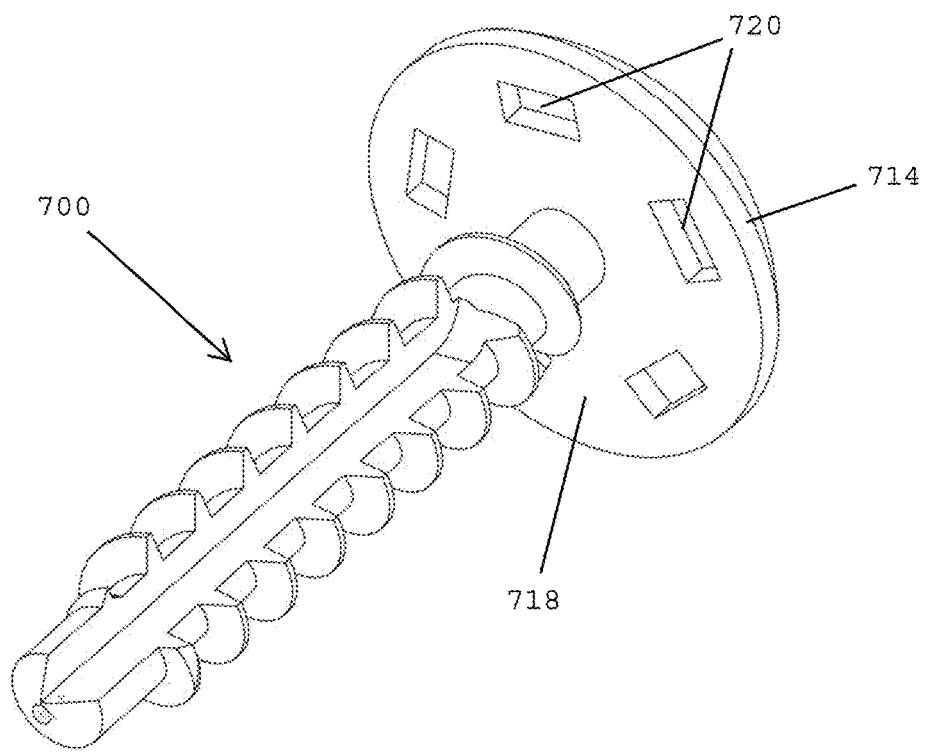
FIG. 20 shows a perspective view of a distal end of a bone screw, in accordance with one embodiment of the present invention.
Figure 21:
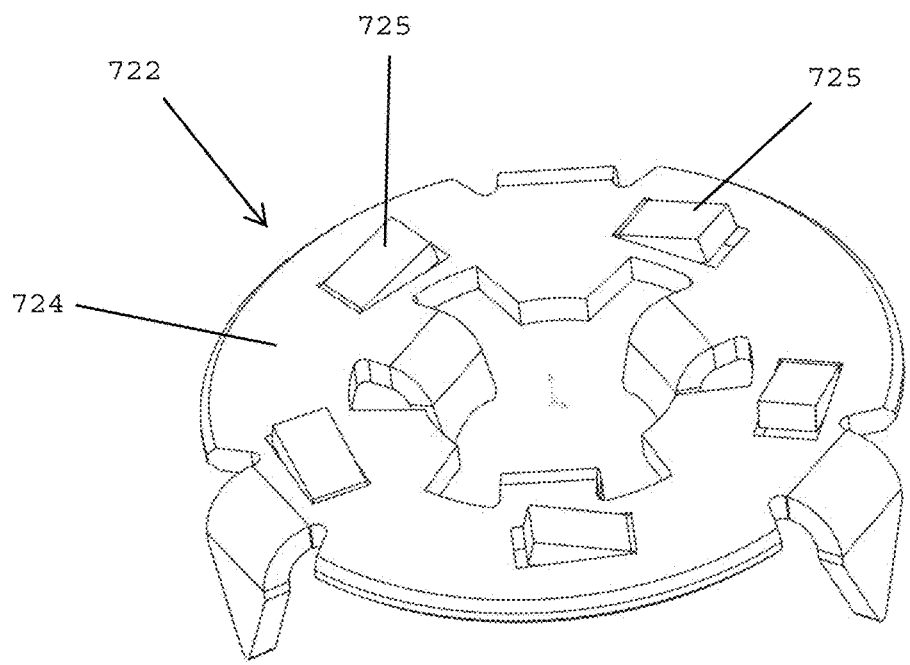
FIG. 21 shows a fastener ring adapted to mate with the bone screw of FIG. 20, in accordance with one embodiment of the present invention.

Referring to FIGS. 20 and 21, in one embodiment, a bone fastener system preferably includes a bone screw 700 having a head 714 with an underside 718 having recesses 720 formed therein.

The bone fastener system desirably includes a fixation plate 722 having a proximal surface 724 with tapered or ramp-shaped protuberances projecting proximally from the proximal face 724. When the bone screw is sufficiently tightened onto the fixation plate 722, the ramp-shaped protuberances 725 on the fixation plate 722 engage with the recesses 720 on the underside 718 of the head 714 for providing the tactile feedback, audible clicking, and prevent loosening of the screw features described above for the embodiment shown in FIGS. 17-19.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A bone screw system comprising:
   a bone screw having a threaded shaft with a proximal end and a distal end, a screw head secured to the proximal end of said threaded shaft, and a tip located at the distal end of said threaded shaft;
   a fixation plate coupled with said threaded shaft, said fixation plate having an outer peripheral edge, a central opening adapted to receive said threaded shaft, and protrusions that extend distally from said fixation plate; and
   an insertion tool having a tubular shaft, wherein said bone screw is disposed within said tubular shaft, and wherein said tubular shaft has a distal shaft section having an inner surface with a groove that seats said outer peripheral edge of said fixation plate for retaining said fixation plate within said distal shaft section, and wherein said fixation plate retained within said distal shaft section of said insertion tool is located at the distal end of said threaded shaft and is spaced from said screw head.

2. The system as claimed in claim 1, wherein said outer peripheral edge of said fixation plate comprises a curved surface.

3. The system as claimed in claim 2, wherein said outer peripheral edge of said fixation plate has a ring shape.

4. The system as claimed in claim 3, wherein said groove seating said outer peripheral edge of said fixation plate comprises a ring-shaped groove.

5. The system as claimed in claim 1, wherein said outer peripheral edge of said fixation plate and said groove seating said outer peripheral edge of said fixation plate form a snap-fit connection for securing said fixation plate at a distal end of said insertion tool.

6. The system as claimed in claim 1, wherein said outer peripheral edge of said fixation plate comprises at least one flat surface.

7. The system as claimed in claim 6, wherein said outer peripheral edge of said fixation plate further comprises at least one curved surface.

8. The system as claimed in claim 1, wherein said tubular shaft of said insertion tool has a circular cross-section.

9. The system as claimed in claim 1, wherein said tip located at the distal end of said threaded shaft of said bone screw comprises a self-tapping tip.

10. The system as claimed in claim 1, wherein said bone screw comprises an elongated groove devoid of threads that extends between the distal and proximal ends of said threaded shaft.

11. The system as claimed in claim 1, wherein said screw head has an underside with malleable protuberances that project toward the distal end of said threaded shaft.

12. The system as claimed in claim 11, said fixation plate further comprising:
 a proximal face that opposes the underside of said screw head; and
 a distal face that faces away from the underside of said screw head, wherein said outer peripheral edge of said fixation plate extends between the proximal and distal faces thereof, and wherein said protrusions are spaced from one another around said outer peripheral edge of said fixation plate and extend distally beyond the distal face of said fixation plate.

13. The system as claimed in claim 12, wherein said spaced protrusions of said fixation plate have lower ends having shapes selected from the group consisting of rounded lower ends, pointed lower ends, sharpened lower ends, oval lower ends, and square lower ends.

14. The system as claimed in claim 12, wherein said distal shaft section of said tubular shaft of said insertion tool comprises a plurality of spaced, elongated slots that extend along the length of said tubular shaft, wherein said spaced, elongated slots are open at a distal-most end of said tubular shaft, and wherein said spaced protrusions of said fixation plate are disposed within said spaced, elongated slots.

15. The system as claimed in claim 1, wherein said tubular shaft has a proximal shaft section having an inner diameter that closely matches an outer diameter of said screw head.

16. The system as claimed in claim 1, wherein the central opening of said fixation plate has an outer perimeter, and wherein said fixation plate further comprises guide flanges positioned around the outer perimeter of the central opening for engaging said threaded shaft of said bone screw.

17. A bone screw system comprising:
 a bone screw having a threaded shaft with a proximal end and a distal end, a screw head secured to the proximal end of said threaded shaft, and a self-tapping tip located at the distal end of said threaded shaft;
 a fixation plate coupled with said threaded shaft, said fixation plate having an outer peripheral edge, a central opening adapted for receiving said threaded shaft of said bone screw, and protrusions that extend distally from said fixation plate, wherein said fixation plate is located at the distal end of said threaded shaft and is spaced from said screw head; and
 an insertion tool having a tubular shaft that extends to a distal end of said insertion tool, wherein said bone screw is disposed within said tubular shaft, and wherein said tubular shaft has a distal shaft section having an inner surface with one or more grooves that seat said outer peripheral edge of said fixation plate for retaining said fixation plate within said distal shaft section.

18. The system as claimed in claim 17, wherein said distal shaft section of said tubular shaft comprises a plurality of spaced, elongated slots that extend along the length of said tubular shaft and that are open at the distal end of said insertion tool, and wherein said spaced protrusions of said fixation plate are disposed within said spaced, elongated slots of said tubular shaft.

19. The system as claimed in claim 17, wherein said outer peripheral edge of said fixation plate has a ring shape, and wherein said one or more grooves of said insertion tool comprises a ring-shaped groove that forms a snap-fit connection with said fixation plate.

20. The system as claimed in claim 16, wherein said outer peripheral edge of said fixation plate comprises at least one straight surface.

21. A bone screw system comprising:
 a bone screw having a threaded shaft with a proximal end and a distal end, a screw head secured to the proximal end of said threaded shaft, and a tip located at the distal end of said threaded shaft;
 a fixation plate coupled with said threaded shaft, said fixation plate having an outer peripheral edge, a central opening adapted to receive said threaded shaft, and protrusions that extend distally from said fixation plate; and
 an insertion tool having a tubular shaft, wherein said bone screw is disposed within said tubular shaft, wherein said tubular shaft has a distal shaft section having an inner surface with a retention structure that seats said outer peripheral edge of said fixation plate for retaining said fixation plate within said distal shaft section, and wherein said fixation plate retained within said distal shaft section of said insertion tool is located at the distal end of said threaded shaft and is spaced from said screw head.

22. The bone screw system as claimed in claim 21, wherein said retention structure is selected from the group consisting of grooves, depressions and rings.

* * * * *